United States Patent
Kendrup et al.

(10) Patent No.: US 11,975,165 B2
(45) Date of Patent: May 7, 2024

(54) DRUG DELIVERY SYSTEM FOR ONE OR MORE ACTIVE INGREDIENTS

(71) Applicant: QPHARMA AB, Malmö (SE)

(72) Inventors: John Ingvar Feldtblad Kendrup, Oxie (SE); Steen Alex Stavnshøj, Simrishamn (SE); Ian Peter Flawn Orpana, Malmö (SE)

(73) Assignee: QPHARMA AB, Malmö (SE)

(*) Notice: Subject to any disclaimer, the term of this patent is extended or adjusted under 35 U.S.C. 154(b) by 757 days.

(21) Appl. No.: 14/900,480

(22) PCT Filed: Sep. 11, 2014

(86) PCT No.: PCT/IB2014/064427
§ 371 (c)(1),
(2) Date: Dec. 21, 2015

(87) PCT Pub. No.: WO2015/036952
PCT Pub. Date: Mar. 9, 2015

(65) Prior Publication Data
US 2016/0136402 A1 May 19, 2016

(30) Foreign Application Priority Data
Sep. 12, 2013 (SE) .................................. 13510516

(51) Int. Cl.
*A61M 31/00* (2006.01)
*A61F 6/08* (2006.01)
*A61F 6/14* (2006.01)

(52) U.S. Cl.
CPC ............ *A61M 31/002* (2013.01); *A61F 6/08* (2013.01); *A61F 6/142* (2013.01); *A61M 2205/04* (2013.01); *A61M 2207/00* (2013.01)

(58) Field of Classification Search
CPC .... A61F 6/06; A61F 6/065; A61F 6/08; A61F 6/12; A61F 6/14; A61F 6/142;
(Continued)

(56) References Cited

U.S. PATENT DOCUMENTS 3,809,076 A * 5/1974 Chabon .................. A61F 6/148
128/839
3,993,072 A * 11/1976 Zaffaroni .................. A61F 6/14
424/430

(Continued)

FOREIGN PATENT DOCUMENTS

EP 2 140 860 A1 1/2010
WO 2012/170578 A1 12/2012

OTHER PUBLICATIONS

Pharmaceutical definition. entry 2. Merriam Webster Dictionary. https://www.merriam-webster.com/dictionary/pharmaceutical (Year: 2021).*

(Continued)

*Primary Examiner* — Caitlin A Carreiro
(74) *Attorney, Agent, or Firm* — Fox Rothschild LLP

(57) ABSTRACT

A drug delivery system that includes an elongated inert support and at least two reservoirs containing a pharmaceutically active ingredient. The inert support has a number of wall segments that define at least two compartments arranged for accommodating the at least two reservoirs. The inert support is made of a material which prevents migration or diffusion of the active ingredient from one reservoir into the other or into the support. Since the drug delivery system is divided into compartments, one for each reservoir containing an active ingredient, the release rates of each active ingredient can be independently controlled or adjusted. This is due to the fact that there is no interaction between the (Continued)

active ingredients, and accordingly the active ingredients will not influence each other physically or chemically.

18 Claims, 7 Drawing Sheets

(58) Field of Classification Search
CPC .......... A61F 6/144; A61F 6/146; A61F 6/148; A61F 6/16; A61F 6/18; A61F 6/22; A61F 6/225; A61K 9/0036; A61K 9/0039; A61K 9/0092; A61K 9/02; A61K 9/025; A61K 9/0068; A61K 9/2072; A61K 9/0004; A61M 31/002; A61M 2207/00; A61M 2207/10; A61M 2205/04
USPC .......................................... 128/830, 832, 833
See application file for complete search history.

(56) References Cited

U.S. PATENT DOCUMENTS

| | | | |
|---|---|---|---|
| 4,012,496 A | 3/1977 | Schopflin et al. | |
| 4,155,991 A | 5/1979 | Schopflin et al. | |
| 4,292,965 A * | 10/1981 | Nash .................... | A61K 9/0036 128/833 |
| 4,304,226 A * | 12/1981 | Drobish ............... | A61K 9/0036 604/93.01 |
| 4,596,576 A | 6/1986 | de Nijs | |
| 4,961,931 A * | 10/1990 | Wong ................... | A61K 9/0036 424/431 |
| 5,972,372 A * | 10/1999 | Saleh ................... | A61K 9/0036 424/422 |
| 6,264,973 B1 | 7/2001 | Mahashabde et al. | |
| 2004/0247674 A1* | 12/2004 | Haapakumpu ....... | A61K 9/0024 424/471 |
| 2007/0043332 A1* | 2/2007 | Malcolm .............. | A61K 9/0036 604/500 |
| 2009/0142313 A1* | 6/2009 | Talling ................... | A61P 15/02 424/93.45 |
| 2009/0149833 A1* | 6/2009 | Cima ................... | A61K 9/0024 604/517 |
| 2011/0146693 A1* | 6/2011 | Duesterberg ......... | A61K 9/0039 128/833 |
| 2012/0004724 A1* | 1/2012 | Hudson ................. | A61L 31/16 623/11.11 |
| 2012/0089122 A1* | 4/2012 | Lee ....................... | A61L 31/148 604/517 |
| 2012/0272969 A1* | 11/2012 | Tjader .................... | A61P 15/08 128/830 |

OTHER PUBLICATIONS

International Search Report and Written Opinion, Appln. No. PCT/IB2014/064427, dated Dec. 5, 2014.
Written Opinion of the International Preliminary Examining Authority, Appl. No. PCT/IB2014/064427, dated Sep. 22, 2015.

* cited by examiner

DRUG DELIVERY SYSTEM FOR ONE OR MORE ACTIVE INGREDIENTS

This application is a 371 filing of International patent application no. PCT/IB2014/064427 filed Sep. 11, 2014, which claims the benefit of Swedish patent application no. 13510516 filed on Sep. 12, 2013.

BACKGROUND

The present invention relates to a drug delivery system, a method of manufacturing said system and the use of said system in a drug delivery device.

The desirability of sustained release drug formulations has long been a goal in the pharmaceutical industry. Sustained release devices solve many of the problems associated with conventional drug delivery devices. For example in conventional drug delivery devices administration of the drug is given frequently and results in high variability in circulating drug levels during the course of treatment. The concentration of the drug increases to therapeutic concentrations after administration, but in some instances the concentration rises above the minimal therapeutic level reaching the toxic threshold. After a relatively short period the drug concentration decreases via metabolisation or excretion to levels that are no longer therapeutic.

In order to achieve constant levels of drugs and avoid the inefficiencies of the drug concentration peaks and valleys the drugs should be released from a delivery device at a rate that does not change with time, so called zero-order release.

Various types of delivery devices have been developed for the controlled and sustained release of active ingredients such as drugs, preferably by diffusion through the surface of the device.

One such device is the intrauterine device (IUD); Mirena® which is considered one of the safest and most efficient contraception used worldwide. In addition to preventing undesired pregnancies, the device provides several advantages: its use is controlled by the female; it allows for a better regulated dose of drug without attention by the user; and it avoids the destruction (by the intestine and by first pass through the liver) of an appreciable portion of the daily dosage of the drugs compared to their orally delivered counterparts.

Other devices commercially available today are the intra vaginal rings (IVRs), e.g. the Estring®, Femring®, and Nuvaring®, or subdermal contraceptive implants, e.g. the Implanon®, all of which provide controlled and sustained release of steroid molecules over a prolonged period, e.g. several weeks/months.

One example of a vaginal ring is disclosed in WO9804220, wherein one or more drug-containing core(s) is positioned in a hollow internal channel of the device. However, since said cores have to be positioned in the device immediately prior to use, this adds complexity, and it is difficult to carry out in a safe manner.

These commercially available IVRs and IUDs, is highly complex and the known manufacturing processes are both labour-intensive and thus expensive. There is therefore a continuous need to provide new manufacturing method for delivery devices for sustained and controlled administration of one or more active ingredients.

Certain therapies or regimens require, or would benefit from, the administration of more than one drug at the same time. This is true for the administration of a variety of medicaments extending from veterinary medicine to human drug administration. One example being in the field of contraception and hormone replacement therapy.

In some cases, the two or more drugs are most effective when they are administered at specified rates relative to each other. Whether the ratio of these specified rates is 1.0 (on a mole or weight basis) or something other than 1.0, deviations from the specified ratio can result in a loss of effectiveness, the inducement of undesirable side effects, or in some cases toxicity.

The placement of a blend of the drugs in a single delivery device in a proportion equal to the desired delivery rate ratio will almost never achieve the desired result. In many cases, the drugs will not diffuse together through the surface or membrane at the same ratio, as they exist in the blend. The ratio would instead be dependent on the inherent ratio of the normalized permeation rates for the drugs through e.g. the rate-controlling membrane. Flexibility would therefore be limited to the selection of suitable polymer candidates for the membrane. Accordingly, the range of, and degree of control over, the delivery rate ratio, is extremely limited.

Of course the need for maintaining a specified delivery rate ratio can be met by using a separate delivery device for each drug. However, this is clearly undesirable, since the presence of two or more delivery devices will compound the disruption which even a single delivery device might create in the normal physiological activity of a animal or human. In addition, if one delivery device malfunctions, the desired delivery ratio will be lost. Further, complete therapy in a single implantable or insertable delivery device is more acceptable to patients and more efficient to insert and remove.

A further problem with the known devices arranged for releasing more than one drug, is that such devices usually show sub-optimum release patterns for the different drugs, whereas it is generally preferred that all drugs are released in a controlled rate during a specified duration of time. Furthermore, since each drug and delivery device combination behaves uniquely, it is not possible simply to exchange one drug with a different drug in the same device, as this could have a significant impact on the drug(s) release characteristics.

U.S. Pat. No. 4,012,496 relate to an intravaginal ring trying to overcome these problems. In said ring the drug containing part of the ring is formed by one or several thin drug matrix strings embedded in and extending from a groove placed along the periphery of the ring. Depending on the particular drug and its release characteristics, the drug string can in some instances be very thin, which gives rise to production-technical problems. Not only will the thin strings limit the amount of active ingredient which can be added to the strings, but the surface area will also be small thereby reducing the drug release of the active ingredients to undesirable levels. Furthermore, since a rate-controlling membrane does not cover the drug strings there is very limiting possibilities to control the release rate and the drugs will influence each other, altering their release profiles undesirable. Another problem with the intravaginal ring in U.S. Pat. No. 4,012,496 is that the drug strings protrude from the supporting ring. Not only will such protruding strings cause discomfort for a patient, they will also have a tendency to separate from the supporting ring, and be a site for undesirable bacterial growth.

U.S. Pat. No. 4,596,576 also disclose the simultaneous administration of several drugs in an intravaginal ring. Said ring consists of two or more compartments which each are separately encased or surrounded by a membrane, which is permeable to the drug. The encased compartments then being assembled together so that one release device (a vaginal ring) is obtained. To achieve a suitable ring with a constant release ratio, it is however necessary to join the ends of the compartments by using inert stoppers, which prevent mixing of the active ingredients. One of the disadvantages of this device is the expensive and complex method of joining the compartment ends to the stoppers, and which makes it difficult to obtain a safe and reliable product.

Thus, there is a demand for a novel drug delivery system, which ensures that the system releases the drug or drugs in a controlled manner and in the correct ratio, and a method for manufacturing the system that is simple, inexpensive and which preferably eliminates the need to make a specific construct for each individual application.

SUMMARY OF THE INVENTION

Thus, it is a first aspect of the present invention to provide a universal delivery system, which can be loaded with one or more active ingredients and where each active ingredient is released at a controlled rate.

In a second aspect according to the present invention is provided a delivery system arranged for administrating two or more drugs at specified rates and/or ratios relative to each another.

In a third aspect according to the present invention is provided a delivery system that eliminates the need to make a specific system for each individual application.

In a forth aspect according to the present invention is provided a delivery system that is inexpensive to manufacture and is simple and reliable to use.

In a fifth aspect according to the present invention is provided a delivery device comprising the delivery system according to the invention, for implantation e.g. subcutaneous or for vaginal or uterine placement in an animal or human.

In a sixth aspect of the present invention is provided a delivery system, which safely and effectively can be inserted into, and removed, from, a patient without causing discomfort.

The novel and unique features whereby these and further aspects are achieved according to the present invention is the fact that the drug delivery system comprises an elongated inert support and at least two reservoirs comprising a pharmaceutically active ingredient. Said inert support comprises a number of wall segments, defining at least two compartments along said support, said compartments are arranged for accommodating the at least two reservoirs.

The inert support is made of a material, which prevents migration and/or diffusion of active ingredient from one reservoir into the support and further into at least one neighbouring reservoir.

Since the drug delivery system is divided into compartments, one for each reservoir containing an active ingredient, the release rates of each active ingredient can be independently controlled and/or adjusted. This is due to the fact that there is no interaction between the active ingredients, and accordingly said active ingredients will not influence each other physically or chemically. Furthermore, when a delivery system is designed for a specific treatment, interactions between the active ingredients in the respective reservoirs need not be assessed, since each reservoir will function as a single, separate delivery system, and the developments costs is accordingly reduced.

In a preferred embodiment the material of the inert support have a lower permeability to the active ingredient than the material of the reservoirs. Thereby is effectively prevented that the active ingredient(s) will, in any substantial degree, diffuse or in any other way migrate from the respective reservoir into the support material.

The term "inert" in the context of the present invention means that material is inert in the sense that it is non-reactive, i.e., the material of the support do not degrade or react with either the active ingredient(s) or the materials of the reservoirs or other elements of the drug delivery system or device.

In order to ensure separation between the individual reservoirs, it is preferred that the compartments of the support are arranged for accommodating the at least two reservoirs without providing an interface between said reservoirs, thereby separating the reservoirs chemically and physically, both during manufacturing and use.

By using a support with several compartments, it is ensured that the delivery system according to the invention can comprise several reservoirs (one in each compartment) each having at least one active ingredient, thereby allowing for a combination treatment. In one embodiment the same active ingredient can be loaded in each reservoir. Alternatively the same active ingredient can be placed in at least one first reservoir, whereas at least one-second reservoir contains a different active ingredient(s) or no active ingredient at all.

The present invention thereby provides a unique means of delivering one, and preferably more than one, active ingredient simultaneously to an environment at a specified ratio of delivery rates. The ratio of delivery rates from the system is preferably arranged such that it remains constant for the duration of use.

Thus, a delivery system having for example four compartments can comprise four different active ingredients, one active ingredient in each reservoir. In a different embodiment, two of said compartments can contain the same active ingredient and the remaining two compartments two different active ingredients. Alternatively, and optionally one or more of the compartments could be loaded with an inert agent, in order to alter the release profile in this way.

In a further embodiment one or more compartments can comprise more than one active ingredient. This is e.g. preferred when the active ingredients does not influence each other negatively, or if the interaction between said active ingredients is known, can be predicted and/or if the interactions is not relevant for the release profile.

In the preferred embodiments the inert support will function as a skeleton, having a number of compartments for accommodating individual and independent reservoirs. This solution is advantageous from a production-point of view, since the use of a universal skeleton will eliminate the need to make a specific support for each individual use, i.e. similar supports can be used for different purposes, thereby reducing the manufacturing costs significantly. Furthermore, since the reservoirs can be placed independently of the other reservoirs in each compartment, it is possible to adjust the release profile of the respective active ingredients simply by adjusting the release profile of the relevant reservoirs, using the same inert support/skeleton.

Independent placement of the respective reservoirs is also beneficial, if the reservoirs influence each other negatively during manufacturing. This could be the situation if one reservoir contains an ingredient, which would alter the effect or behaviour of an ingredient in a different reservoir, e.g. because one ingredient would poison the other, before the respective reservoirs e.g. are cured/cooled/hardened. Thus, by using the system of the present invention, it is possible to use materials in the reservoirs which otherwise would be considered incompatible from a production perspective, and which up to now would have been very difficult, if not impossible, to include in a single delivery system, without extensive manufacturing costs and without compromising the safety of the system.

In a preferred embodiment the wall segments are substantially plate like structures each circumferentially extending from a common axis of the support, and preferable in the complete length of the supports axis. As the wall segments are spaced apart, the compartments are axially displaced and substantially arranged longitudinally along the axis, i.e. around the circumference of the axis, and extending in the length of the support. In one embodiment the wall segments is evenly distributed along the longitudinal axis of the support, in a different embodiment the segments are unevenly distributed.

In this way a very simple and inexpensive support can be obtained, where it is ensured that the different reservoirs are physically separated from each other, such that the active ingredient placed in the reservoirs cannot interact with each other during manufacturing and/or use. Accordingly the release profile of the respective active ingredient will not be influenced by the presences of other active ingredients, and each reservoir will in practice function as a single, separate delivery system. This will also reduce problems associated with interactions of the active ingredients during e.g. storage. Accordingly, the system according to the invention has an intrinsically safe design, since neither the active ingredients nor other materials in the reservoirs, negatively can influence each other e.g. by altering the desired release profiles.

In a preferred embodiment the inert support has a cross-section in the form of an I, T, Y, H, or X, providing different skeletons for the support. However, a person skilled in the art will understand that the support in principal can have any cross-sectional design, and can have any desired number of compartments, the only requirement being that the inert support is arranged for preventing any physically or chemically interaction between the reservoirs.

The choice of number of compartments and the desired cross-section of the inert support will in any given case depend on the number of active ingredients contemplated for a specific treatment, together with the desired ratio of delivery rates of the active ingredient in the reservoirs, and it will be understood that the skeleton in principal can have any kind of profile and/or cross section as long as the active ingredients in the reservoirs cannot interact. In this way the present invention resides in a unique means of delivering one, and preferably two or more, active ingredient(s) simultaneously to an environment at a specified ratio of delivery rates.

Preferably, the number of compartments will correspond to the number of wall segments. It is preferred that the support comprises two, three, four or five wall segments, thereby defining two to five compartments as this has proven to provide a highly advantageously number of compartments, meeting the demands for combined administration of more than one active ingredient. However, more or less compartments are also contemplated within the scope of the present invention, if this is considered beneficial for other applications.

In a preferred embodiment one or more of the reservoirs is filled with the same material as the inert support, i.e. the reservoir(s) without a pharmaceutically active ingredient becomes an integral part of the inert support, such that one or more of the compartments for accommodating a reservoir in reality are not provided during the manufacturing process. As the material for the inert support in a preferred embodiment is made of a material which is less expensive than the materials of the reservoirs, such a solution will provide a very simply and inexpensive way of providing a system having one or more reservoirs without any active ingredient(s).

Suitable materials for the inert support, which ensures that the active ingredient(s) cannot, to any substantial degree, diffuse or in any other way migrate from the respective reservoir into the support material, and further into the neighbouring reservoirs are preferably a first polymeric material e.g. an inert thermoset or thermoplastic.

It is however, preferred that the first polymer material for the inert support is selected from the group comprising ethylvinylacetate (EVA), thermoplastic polyurethanes (TPUs), polyethylene (PE), polypropylene (PP), polyamide-imide (PAI), polyamide (PA), cross-linked polyethylene (PEX), Thermoplastic elastomers (TPE), thermoplastic vulcanizates (TPVs), Polybutylene terephthalate (PBT), Polyester, poly(ethylene terephthalate) (PET) and copolymers made with one or more of the above materials. Furthermore, other inert materials capable of preventing migration and/or diffusion of the active ingredient through the support are also contemplated for the inert support according to the invention. The inert support is preferably not made of silicone (polydimethylsiloxane), as said material is not capable of effectively preventing migration and/or diffusion.

It will be understood that the permeability of the support materials can be adjusted by known means, e.g. by varying the degree of crosslinking, and/or by using block copolymers and/or by varying the relative amounts of the different blocks, and/or by addition of other materials/compounds, such that the support material can be arranged for preventing migration and/or diffusion of the active ingredient through the support.

The delivery system according to the invention preferably has a substantially annular cross section, transverse to the longitudinal axis, e.g. a circular, oval or ellipse cross section, although other cross sections are contemplated as well. While the diameter, or other appropriate dimension for cross sections other than annular, can vary along the length of the system, it is generally most convenient to use a uniform external diameter, or at least a substantially uniform external diameter, for the entire length of the system.

It is further advantageously that the delivery system, has a relatively smooth outer surface, without any extensions, projections, transitions or edges, which could cause discomfort when a delivery device comprising the system according to the invention is inserted into, or removed from, a patient. It is in this way preferred that the respective reservoirs does not extend beyond the wall segments of the inert support, i.e. that the reservoirs are held within the boundaries of the inert support, such that the reservoirs outer surface does not extend beyond the end surfaces of the wall segments. Preferably at least one reservoir flushes with the end surfaces of the wall segments. Accordingly, it is possible to provide a drug delivery system without any edges or similar noticeable transitions between the inert support and the reservoirs, such that a smooth surface can be obtained both with or without a membrane. This will not only provide a more comfortable drug delivery system, but it will also prevent that the reservoirs can get caught or snagged on something, a risk that is probably if the reservoirs extend out from and beyond the support. Furthermore, drug release properties are better controlled when the reservoirs is held within the boundaries of the inert support. This construction will also prevent any undesirable bacterial growth in the projections and/or transitions and ensure that the reservoirs are retained more securely in the inert support.

Each reservoir positioned in a corresponding compartment will define a "surface area", i.e. an outer surface through which the active ingredients can diffuse/migrate into the surroundings. Accordingly the size of said surface area will influence the release profile of a respective active ingredient. The surface area can be varied by e.g. varying the length of the compartment along the longitudinal axis of the inert support, and/or by adjusting the size of the reservoir in the cross sectional plane.

It is preferred that the surface area corresponds to the size of the respective reservoirs placed in a compartment in the support, thus when the system have a cross section in the form of a circle, the surface area of the reservoirs, not in contact with the wall segments, will also have a cross section corresponding to part of a circle.

The different reservoirs can in one embodiment have substantially identical surface areas for diffusion of the active ingredient(s). However, in another embodiment the surface area of one reservoir may be smaller or larger than one or more of the other reservoirs. In this way it will be possible to adjust the release profile even further, such that it is possible to release e.g. one active ingredient to the surroundings in an even smaller concentration than the other active ingredients. The opposite is of course also possible. The easiest way of obtaining smaller or larger surface areas, is simply to adjust the size of the compartment for accommodation the reservoir, e.g. by adding a wall segment or by placing two wall segments closer together, or by adjusting the size of the reservoir itself.

The reservoirs used in the present invention can be any kind of system capable of releasing an active ingredient, however it is preferred that the reservoirs are formed from a biocompatible polymer, and that the active ingredients are released by diffusion through the polymer.

In one preferred embodiment according to the invention the active ingredient is e.g. uniformly dispersed or dissolved throughout a polymer matrix (monolithic system). In a different embodiment the active ingredient may be confined to an inner core (core system). Both systems are well known in the art and will not be discussed in further details in this application, however it is preferred that the reservoirs of the present invention is arranged for providing sustained delivery of an active ingredient in a substantially zero order release profile.

By substantially zero order it is meant that a substantially constant amount of active ingredient is released over a given period of time. Preferably, the initial dose of a drug is the therapeutic dose, which is maintained by the delivery system, thereby providing a more reliable release rate and a lower initial burst, than hitherto known.

In some embodiments, the delivery system exhibit a substantially zero order release profile of the active ingredient over at least one week, over at least one month, over more than a month or over more than one year.

Irrespectively of the kind of reservoir used for the delivery system, the release profile of the active ingredient(s) can be adjusted further if the drug delivery system comprises at least one rate-controlling membrane. Said membrane may cover all or some of the system. In one preferred embodiment each reservoir comprises an individual membrane, specifically constructed to meet the demands of a desired release profile.

In this way the release of the active ingredient(s) to the surroundings is dependent upon permeation (i.e., molecular dissolution and subsequent diffusion) of the active ingredient(s) not only though the reservoirs surface area but also through the rate-controlling membrane, preferably providing a more reliable release profile, with lower or no initial burst.

It is preferred that the permeability of the membrane can be adjusted, e.g. by using different materials for the membrane, by varying the degree of crosslinking, or by using block copolymers and/or by varying the relative amounts of the different blocks.

The term "permeability" refers to the rate at which permeating ingredients (e.g., active ingredient) pass through the material of an element, e.g. membrane, reservoir or inert support, independently of the thickness or surface area. Permeability in this sense is thus measured per unit volume of the material from which the element is constructed.

In order to prevent the active ingredient(s) from diffusing and/or migrating through the membrane into one or more of the other reservoirs, an extension having the same thickness as the membrane, can be placed on the end-surface of the wall segments of the inert support, in order to physically separate the membranes from each other. This can e.g. be relevant if a specific membrane has a high permeability, and therefore allows diffusion/migration of the active ingredient though the membranes and into the neighbouring reservoirs.

It is known that the release rate of the active ingredient decreases, as active ingredient(s) that is deeper inside the reservoir must diffuse to the surface, since it has farther to travel, and the quadratic relation between distance and time therefore becomes important. Using a rate-controlling membrane with a lower permeability, the impact of the longer travel distance decreases. Thereby is obtained a drug delivery system where the release rate at steady state decreases much more slowly than with conventional devices in the art. This can be obtained in an even higher degree if individual membranes are used for the respective reservoirs.

Preferred examples of adjusting the permeability of the membrane is disclosed in the applicants own patent application no. SE 1350155-6 (published as WO2014122563).

The thickness of the rate-controlling membrane can also be varied to further control the release rate of the active ingredient(s), e.g. by decreasing the release rate of the active ingredient. The term "membrane thickness" refers to the thickness of the rate-controlling membrane averaged over the entire membrane associated with any single reservoir. If the membrane thickness is uniform for a single reservoir, the term denotes the thickness at any point. If the thickness varies, for example by increasing from one end of the reservoir to the other, the term denotes the thickness averaged over the entire permeable surface of the rate-controlling membrane of the reservoir.

The delivery system according to the invention is capable of releasing one or more active ingredient in a controlled manner and in the correct mutual ratio. This is achieved because each reservoir resembles an independent delivery system. The release profile of each reservoir can be independently adjusted or controlled by varying one or more of the following parameters:
  amount/concentration of active ingredient in a reservoir,
  number of reservoirs containing the same or different active ingredient,
  use of reservoir(s) with no active ingredient,
  the surface area and volume of each reservoir,
  permeability of the reservoir,
  use of rate-controlling membranes, size, thickness and shape of the inert support, e.g. the wall segments,
permeability of the membrane, and
thickness of the individual membrane.

The parameters may be varied singly or in combination, and further variations may also be incorporated, such as the length of the respective reservoirs and the size of the delivery system used in the final delivery device.

Control of the delivery rates is thus transferred to a number of easily adjustable parameters, which provide a full range of flexibility and variation, rather than relying on the quantities, concentrations, and ratios of the active ingredients alone. Thereby is obtained a very effective and inexpensive drug delivery system, in which the active ingredients are released in a more controlled manner than hitherto known.

In this way the present invention have an intrinsically safe design, since it is possible to administer two or more active ingredient e.g. drugs, at specified rates relative to each another, thereby preventing loss of effectiveness and the inducement of undesirable side effects, which is known with the commercially known devices.

As specified above, it is possible to also incorporate a reservoir without active ingredient into one or more of the compartments of the delivery device. Accordingly release of active material from such reservoirs cannot take place, and the release profile of the system can be further adjusted.

In order to ensure that the reservoirs are retained securely in place in the compartments, it is preferred that the reservoirs are not thin circular/annular strings, i.e. strings which is embedded less than about 50% into the support. Preferred form/shapes of the reservoir is reservoirs that increases its width the closer the reservoir is to the longitudinal axis of the inert support. This further increase the ability to adhere to the skeleton and further control the release of active ingredient. Preferred reservoirs are also reservoirs having shapes with edges and/or straight sides, since such shapes also will have a better ability to adhere to the sides of the inert support. It will be understood that the respective compartments of the inert support have a shape complementary to the reservoir and vice versa.

In an advantageously embodiment at least one of the wall segments comprises at least one first retention means for securing at least one reservoir in the corresponding compartment. The addition such a retention means is preferably when the reservoir and the inert support are not immediate compatible or when it is problematic to maintain the reservoir in the correct position in the compartment, e.g. because the reservoir will not adhere securely to the support.

The first retention means is preferably placed on the side-surfaces of the wall segments facing the reservoir. Any kind of retention means capable of securing the reservoir to the inert support is contemplated within the scope of the present invention, but in a preferred embodiment the first retention means are in the form of elongated hooks and/or barbs and/or in the form of irregular surfaces.

In a different embodiment the inert support comprises at least one second retention means, for securing the reservoir and/or a rate-controlling membrane to the inert support. The second retention means is preferably a projection placed on the end-surface of at least one of the wall segments. In order to have a substantially annular cross section of the delivery system, said projections preferably have a cross sectional form of a fraction of a circle, corresponding to the dimensions of the inert support, the reservoirs and optionally the membranes. In this way the projection will partly cover the reservoirs and optionally one or more membranes, in such a way that all elements are securely held in place. It is preferred that the projection can cover the reservoirs/membranes in varying degrees, thereby providing an additional way of adjusting the release rates of the different active ingredient in the respective reservoirs.

The first and second retention means is preferably an integral part of the wall segments, made of the same material as the inert support and preferably simultaneously with said support, thereby providing a very simple and inexpensive design. However the retentions means can also be retrofitted, e.g. by gluing or melting.

Alternatively, the rate-controlling membranes can be arranged for being embedded into the end-surfaces of the wall segments, by at least one third retention means, thereby securing at least one reservoir and at least one membrane to the inert support. However, if a membrane covers the entire longitudinal surface of the delivery system, then said membrane will retain the reservoirs in place, and the need for retention means is of lesser importance, but might still be relevant for securing the reservoirs and membranes to the support during the manufacturing process.

In an alternative embodiment, the reservoirs are held securely in place by the shape of the compartment. This is e.g. possible using an overall H-shape, providing two compartments between the legs of the H. If the compartments are wider at the base, (i.e. closest to the longitudinal axis of the inert support) than at the opening, (i.e. at the surface area not in contact with the inert support), the reservoirs can easily be retained in the respective compartment, without any additional means.

It is preferred that the delivery system according to the present invention is incorporated into a drug delivery device. Such a device can have a wide range of shapes, sizes and forms for delivering the active ingredients/drug(s) to different environments of use, however it is preferred that the system is incorporated into a drug delivery device, in the form of an implant, an intrauterine device (IUD), or an intravaginal ring (IVR). Such delivery system might consist either completely (e.g. an IVR, or implant) or partly (e.g. an IUD, or implant) of the delivery system according to the invention.

The polymeric materials used for the reservoirs and membranes when the delivery system is used in an IUD, IVR or implant of the present invention are preferably suitable for placement in the body, i.e., they are non-toxic and non-absorbable in the patient. In this respect a variety of inert thermoset or thermoplastic materials are contemplated.

It is however preferred that the polymer material of the reservoirs and the membranes is a thermosetting elastomer, especially a silicone polymer, as experiments have shown that these materials provides especially advantageously reduced release rates, and substantially no initial burst. Furthermore, silicone elastomers, such as poly(dimethylsiloxane) has proven to be highly suitable for providing delivery of an active ingredient in a substantially zero order release profile, and such silicones are already used conventionally for IVRs. However, silicone polymers with functional groups of phenyl-, flouro-, chloro-, butyl-groups and the like, are also contemplated within the scope of the present invention.

However, in other embodiments the polymers of the membrane and reservoirs can be a second thermoplastic polymer suitable for pharmaceutical use, such as cellulose acetate butyrate, cellulose acetate propionate, cellulose acetate, ethyl cellulose, polyvinyl acetate (PVA), poly(ethylene-co-methyl acrylate), ethylene-vinyl acetate (EVA), poly(methyl methacrylate), thermoplastic vulcanizates (TPVs), and thermoplastic polyurethanes (TPUs), including copolymers thereof.

In a preferred embodiment the inert support is made of a first thermoplastic material, the reservoirs are made of a thermoset silicone, and the membrane(s) are made of a thermoset silicone or a second thermoplastic material. In a different embodiment the inert support, the reservoir and the one or more membranes are all made of a thermoplastic material, preferably different materials.

It will be understood that the inert support, the reservoir and the membranes can be made of the same or a different material, as long as the inert support substantially prevents migration and/or diffusion of active ingredient from one reservoir into the support and further into at least one neighbouring reservoir. In a preferred embodiment this is obtained by ensuring that the permeability of the inert support is lower than that of the reservoirs, e.g. by varying the degree of cross linking, by using block copolymers and/or by varying the relative amounts of the different blocks materials in the respective material.

The IUD, implant and IVR according to the invention can have any conventional shape, the only requirement being that the IUD and IVR should be flexible enough to enable bending and insertion inside the uterus or the vaginal cavity, and rigid enough to withstand the expulsive forces of the musculature without causing abrasion to the epithelium.

A force balance thus exists between the elastic recoil of e.g. the IVR and the musculature of the vaginal wall, with dimensions and material elastic modulus determining the final conformation and retention of the IVR. This also means that an IVR made of materials having a low elastic modulus require a wider cross-sectional diameter in order to obtain the desired ring stiffness.

In one preferred embodiment according to the present invention, the elastic modulus of the system is defined by the elastic modulus of the inert support. That is, the elastic modulus, i.e. the stiffness of the elastic material also known as Young's modulus, is substantially defined by the inert support. Accordingly, the elastic modulus of the reservoirs and membranes is less significant, whereby the materials of the reservoirs and membrane can be selected based on e.g. desired release patterns alone. Furthermore, as the stiffness to the inert support can be selected based on desired parameters of the delivery system, the dimensions of the device can also be chosen in order to obtain optimal user acceptability. Thus when the stiffness/rigidity of the system is allocated substantially to the inert support, the elastic modulus parameter of the reservoirs and membranes can be factored out of the development process, thereby reducing development complexity, and manufacturing costs.

The dimensions of the IVR may vary depending upon the anatomy of the subject, the amount of drug(s) to be delivered to the patient, the time over which the drug(s) is to be delivered, the diffusion characteristics of the drug and other manufacturing considerations. In the context of the present invention the term intravaginal ring, also contemplates ring designs or structures, which have other shapes, e.g. polygonal shapes and/or wavy shapes, or where the structure is not a complete and/or closed circle/shape.

The system of the present invention is preferably arranged for administrating one or more active ingredient(s). Said active ingredients are preferably in a crystalline, dissolved or amorphous form in said reservoir, and can in principal be any kind of locally or systematically active medicament/drug.

It is however preferred that the active ingredients is at least one steroid, e.g. contraceptive agents such as an estrogenic steroid, and a progestational steroid, where the estrogenic steroid is placed in one reservoir and the estrogenic steroid in another reservoir. In a preferred embodiment the active ingredient is a combination of estradiol with progestogen selected from the group consisting of etonogestrel, nestorone, levonorgestrel, d-1-norestrel and norethindrone, preferably levonorgestrel. However the steroids can also be selected in order to treat other conditions, e.g. vaginal atrophy and symptoms associated with menopause, e.g. hot flashes.

As an example can be mentioned, that if e.g. estradiol is combined with etonogestrel or nestorone it is preferred that estradiol is released from its reservoir in a concentration which is about 10 times lower than the concentration released from the reservoir containing etonogestrel or nestorone, respectively.

In a different embodiment the active ingredient may be a spermicides, an antimicrobial agent, an anti-viral agent or an anti-HIV agent. Such agents are well known in the art and will not be discussed in greater details in this application.

It is however a preferred, to provide a combination product in accordance with the "multipurpose prevention technology" comprising both contraceptive agents and active agents having a different purpose, e.g. anti-HIV agents. Such a product would be highly relevant in developing country having problems with both undesired pregnancies and HIV-infections.

Irrespectively of the active ingredient or the intended use of the system, the delivery system according to the invention is adapted to deliver pharmaceutically effective amounts of active ingredient(s). By "pharmaceutically effective," it is meant an amount, which is sufficient to effect the desired physiological or pharmacological change in the subject. This amount will vary depending upon such factors as the potency of the particular ingredient, the desired physiological or pharmacological effect, and the time span of the intended treatment. Those skilled in the arts will be able to determine the pharmaceutically effective amount for any given active ingredient(s) in accordance with standard procedures.

The present invention also relates to a method of manufacturing the delivery system according to the present invention.

Said manufacturing method comprises the following steps:
a) provide an inert support with two or more wall segments, defining at least two compartments along said support, and
b) placing one reservoir in each compartment, without providing an interface between said reservoirs.

Preferably all the reservoirs are placed on the support simultaneously. If the drug delivery system also comprises one or more rate controlling membranes said membranes is thereafter placed on the support/reservoir structure, preferably simultaneously.

The respective steps of the method according to the invention can be obtained by any known means, e.g. extrusion or injection moulding.

In a preferred embodiment the inert support, the reservoirs and the at least one membrane are extruded using "sequential extrusion". However, the reservoirs and membranes can also be made in the same step, i.e. they can be co-extruded. This is especially preferred when the reservoirs and membranes are made of the same class of material.

Depending on the materials used for the inert support, the reservoirs and the membranes, curing or cooling steps might be provided between each step. As one example can be mentioned, that the inert support can be cooled before the reservoirs are placed in the support, e.g. with cool air or in a cooling bath, in order to ensure that the support has the desired rigidity to fully support/sustain the reservoirs. This is relevant especially when the reservoirs are made of a silicone polymer, as said polymer cures slow and lacks strength before curing/cooling. When the reservoirs are made of silicone, said reservoirs might be heated mildly for achieving a faster curing. The same is the situation when the membranes are made of silicone. If the membrane(s) instead is made of thermoplastic, the membrane can preferably be cooled in order to obtain the desired solidity and accordingly strength.

The inert support/skeleton preferably provides a fundament for attachment of the reservoirs during manufacturing, and it is therefore preferred that said inert support/skeleton has a sufficient elastic modulus i.e. stiffness, in order to support the reservoirs until they have cured. Furthermore, it is also possible to ensure that the final stiffness of the system meets the demands of the user, by changing the elastic modulus of the inert support. Altering the elastic modulus of the support can e.g. be obtained by adjusting the dimensions of the support, e.g. the thickness of the supports axis and/or the wall segments, by using polymers having a higher elastic modulus, or by any other means known to the person skilled in the art.

Using an inert support, which does not provide an interface between said reservoirs is beneficial if the reservoirs otherwise, would influence each other negatively during the manufacturing process. This could e.g. be the situation if one reservoir contains platinum catalysed silicone and a second reservoir contains tin catalysed silicone. In this situation the tin would poison the platinum catalyst, if the reservoirs comes into contact before the reservoirs have cured. Accordingly, the manufacturing process of the present invention ensures that it is possible to include several reservoirs with materials which would otherwise be considered to be incompatible and which up to now would have been very difficult, if not impossible, to manufacture in a single delivery system.

Injection moulding and the extrusion technology are well known in the art and will not be discussed further in this application. The same is the situation with the curing properties for the materials used in the present invention.

When the delivery device is an IVR, the delivery system according to the invention, is preferably first manufactured into long filaments. It is then possible to cut a desired length of said filament, bent the thereby obtained segment into a ring, and connect the two ends to one another by known means, e.g. by gluing or melting the ends together.

When the delivery device is an IUD, the delivery system may be manufactured by initially forming the upper and lower portions of a conventional T-frame, e.g. using injection moulding. The delivery system according to the present invention is then securely attached to the upper and lower portions of the T-frame e.g. by gluing or melting, such that the middle steam of the T-frame is constituted by said delivery system. If the system comprises a membrane, said membrane can be extruded in a separate process, and cured by known means, after which the membrane is cut into desired lengths and placed onto the delivery system and optionally part of the upper and lower portions of the T-frame. The membrane can in a preferred embodiment be placed on the system by stretching the membrane while putting it in place. The membrane then stays in place since is squeezes the delivery system.

BRIEF DESCRIPTION OF THE DRAWINGS

The invention will be explained in greater detail below, describing only exemplary embodiments of the delivery system according to the invention, in which.

DETAILED DESCRIPTION OF THE INVENTION

The present invention relates to a drug delivery device e.g. in the form of an intravaginal ring or a hormone spiral, comprising a delivery system 1, having an elongated inert support and a number of reservoirs comprising a pharmaceutically active ingredient.

Figures 1, 2:
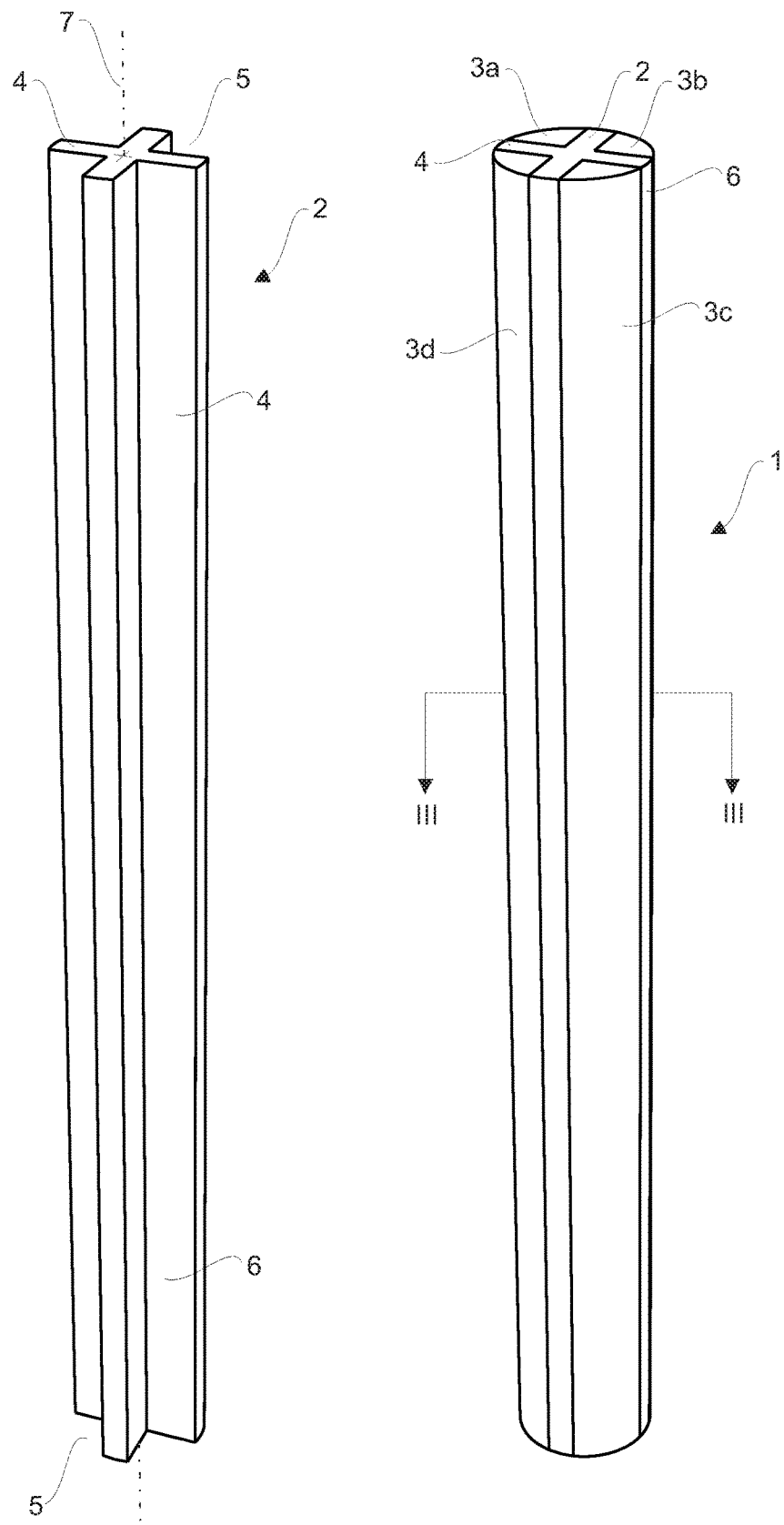
FIG. 1 shows a perspective view perspective view of an elongated inert support, according to the present invention.
FIG. 2 shows a section of an intravaginal ring according to a first embodiment of a delivery system according to the present invention.

FIG. 1 shows a perspective view of an elongated inert support 2, for use in the present invention. Said support has the form of an "X" and accordingly comprises four wall segments 4, defining four compartments 5 along the support. Said compartments are arranged for accommodating four reservoirs having an active ingredient, without providing an interface between said reservoirs.

The wall segments 4 are substantially plate like structures 6 each circumferentially extending from a common axis 7 of the support, and in the complete length of the supports axis. As the wall segments 4 are spaced apart, the compartments 5 are axially displaced and substantially arranged longitudinally along the axis, i.e. around the circumference of the axis 7, and extending in the length of the support.

Figure 3:
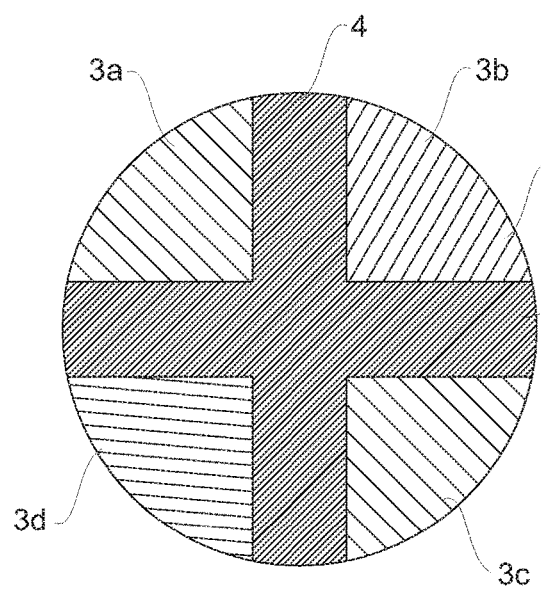
FIG. 3 is a cross-sectional view of the embodiment shown in FIG. 2 taken along the line III-III.

FIG. 2 shows a first embodiment of a delivery system 1 according to the present invention, comprising the inert support of FIG. 1 and four reservoirs 3; 3a, 3b, 3c, 3d. FIG. 3 is a cross-sectional view of the same embodiment, taken along the line III-III of FIG. 2. In said embodiment the four reservoirs 3a, 3b, 3c, 3d, have been attached to the support 2 shown in FIG. 1, one reservoir in each compartment 5. The reservoirs 3a and 3c comprises identical active ingredients, whereas the reservoirs 3b and 3d contains an individual active ingredient, i.e. the active ingredients in reservoirs 3b and 3d is not identical to each other or to the active ingredients in reservoirs 3a and 3c.

As is evident from FIGS. 2 and 3, the reservoirs 3a, 3b, 3c, 3d are physically separated from each other, by means of the inert support 2, i.e. the active ingredients placed in the reservoirs cannot interact with each other, since the support prevents any contact between the reservoirs. Accordingly the release profile of the active ingredient in reservoir 3a will not be influenced by the presences of the active ingredients in reservoirs 3b, 3c and 3d, and vice versa. Each reservoir 3a, 3b, 3c, 3d will therefore in practice function as a single, separate delivery system. Accordingly, the release rates of each active ingredient can be independently controlled and/or adjusted.

Furthermore, it is clear from FIGS. 2 and 3, that the reservoirs 3a, 3b, 3c, 3d does not extend beyond the wall segments of the inert support, i.e. that the reservoirs are held within the boundaries of the inert support 2, such that the reservoirs outer surface does not extend beyond the end surfaces of the wall segments. Accordingly, a drug delivery system is provided without any edges or similar noticeable transitions between the inert support and the reservoirs, such that a smooth surface can be obtained.

In the following other preferred cross sections, which can be used in a delivery system 1 according to the invention, will be discussed. The same reference numbers will be used for identical parts.

Figure 4:
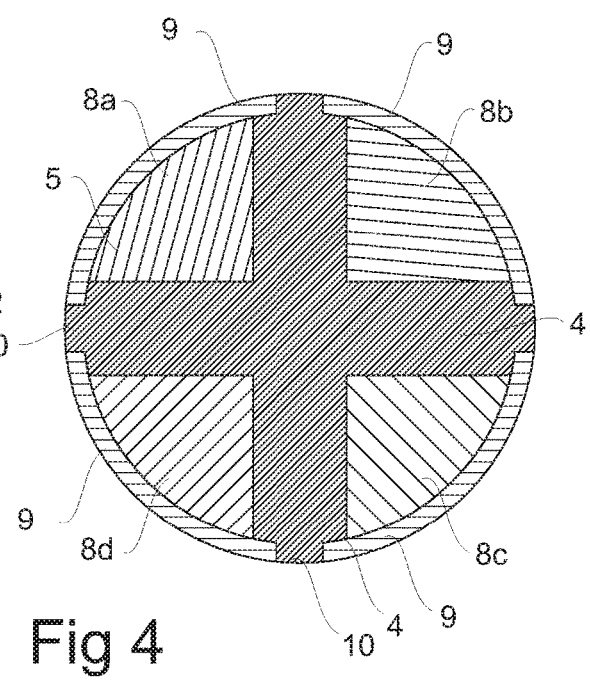
FIG. 4 shows a cross-sectional view of a second embodiment of a delivery system according to the present invention.

FIG. 4 shows a cross-sectional view of a second embodiment of a delivery system according to the present invention. Said embodiment also comprises four reservoirs 8; 8a, 8b, 8c, 8d but each reservoir contains an individual active ingredient. A rate-controlling membrane 9 further covers each reservoir. In the embodiment shown the rate-controlling membrane is identical for all reservoirs 8a, 8b, 8c, 8d, but each membrane 9 is separated from neighbouring membranes and reservoirs, by a small extension 10 made in the end-surface 4' of each wall segment 4. Said extensions 10 have a thickness corresponding to the thickness of the membranes 9, in order to provide a smooth surface of the system. The extensions 10 are preferably manufactured simultaneously with the inert support, and are therefore an integral part of the inert support 2.

By using a rate-controlling membrane 9 the release of the active ingredient(s) to the surroundings is dependent upon permeation (i.e., molecular dissolution and subsequent diffusion) of the active ingredient(s) not only through the reservoir 8, but also through the rate-controlling membranes 9. Separation of the membranes by the extension 10 is further beneficial in order to prevent the active ingredient from diffusing and/or migrating through the membrane into one or more of the other reservoirs, e.g. if the membrane has a high permeability for one or more of the active ingredients.

Figure 5:
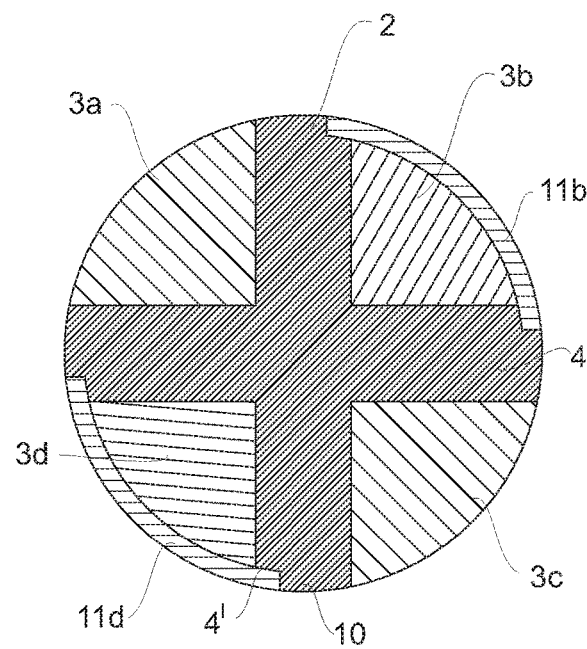
FIG. 5 shows a cross-sectional view of a third embodiment of a delivery system according to the present invention.

FIG. 5 shows a cross-sectional view of a third embodiment of a delivery system according to the present invention. In this embodiment, the respective reservoirs 3 corresponds to the reservoirs shown in FIGS. 2 and 3, i.e. reservoirs 3a and 3c comprises identical active ingredients, whereas reservoirs 3b and 3d contains an individual active ingredient. However, where the reservoirs in FIGS. 2 and 3 has surface areas that allows direct diffusion of the active ingredients into the surroundings, rate-controlling membranes 11b, 11d covers reservoir 3b and 3d, respectively. Thereby is provided a completely different release pattern for the same active ingredients, as for the embodiment shown in FIGS. 2 and 3. Accordingly, the release profile can be adjusted or controlled simply by changing a few parameter, i.e. by introducing rate-controlling membranes 11b, 11d for two reservoirs. It is evident based on the present application that further combinations easily can be made, e.g. by using more membranes, by using membranes for other reservoirs, etc.

Small extensions 10 are made on the end-surface 4' of each wall segment 4, thereby preventing the active ingredients from diffusing and/or migrating through the respective membranes into the other reservoirs.

Figure 6:
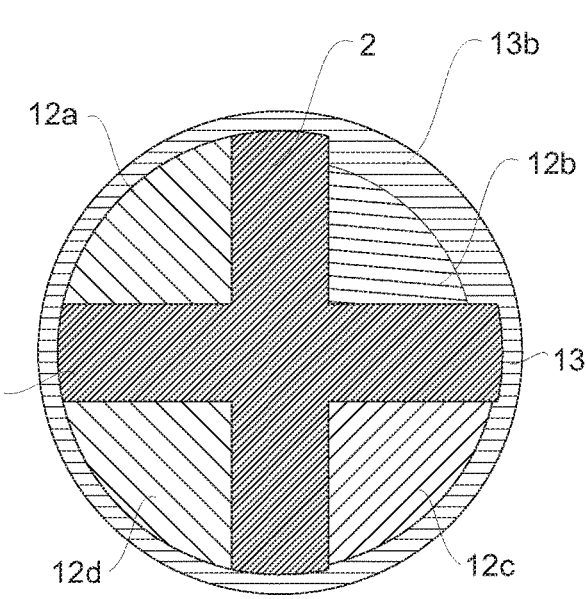
FIG. 6 shows a cross-sectional view of a forth embodiment of a delivery system according to the present invention.

FIG. 6 shows a cross-sectional view of a forth embodiment of a delivery system according to the present invention. In this embodiment the two reservoirs 12a and 12d comprises identical active ingredients, whereas reservoirs 12b and 12c contains individual active ingredient. One rate-controlling membrane 13 covers the entire longitudinal surface of the delivery system, but the thickness of the rate-controlling membrane 13b for reservoir 12b is larger than for the other three reservoirs, in order to reduce the release rate of the active ingredient in reservoir 12b.

Figure 7:
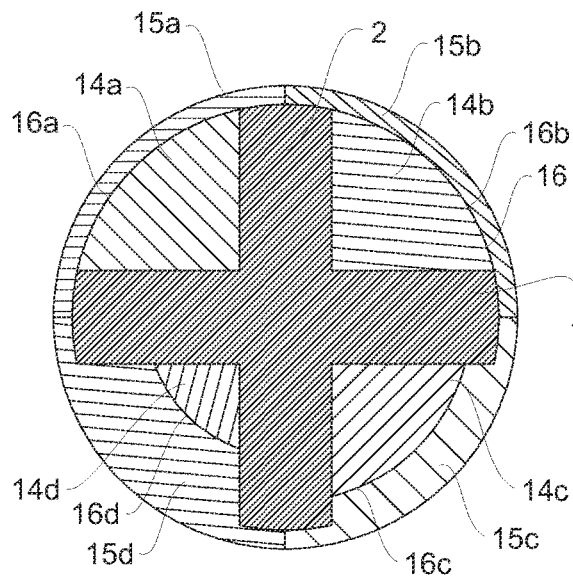
FIG. 7 shows a cross-sectional view of a fifth embodiment of a delivery system according to the present invention.

A similar situation is shown for the fifth embodiment in FIG. 7. In said embodiment each of the four reservoirs 14, i.e. 14a, 14b, 14c, and 14d comprises an individual active ingredient, and each reservoir is further covered by an individual rate-controlling membrane 15a, 15b, 15c, and 15d. Each rate-controlling membrane has an individual permeability, which can be obtained by e.g. using different materials for the membrane, by varying the degree of cross linking, by using block copolymers and/or by varying the relative amounts of the different blocks materials.

Another option is to adjust the thickness of the respective membranes, either alone or in combination with the above. As can be seen in the FIG. 7, membrane 15c is thicker than membrane 15a and 15b, which has an identical thickness, but still thinner than membrane 15d, which is the thickest membrane in the present embodiment. It will be understood by a person skilled in the art, that membranes with different thickness can control the release rates, as the active ingredient will have to travel a longer distances using a thick membrane than a thinner membrane.

Each reservoir will define a "surface area", i.e. an outer surface 16 through which the active ingredients can diffuse/migrate into the membrane and further into the surrounding environment. Accordingly the size of said surface area will influence the release profile of a respective active ingredient.

As can be seen in FIG. 7, the surface area 16c and 16d of the reservoirs 14c and 14d, i.e. the reservoirs with the "thick" membranes is smaller than the surface area 16a and 16b, of the reservoirs 14a and 14b, having thinner membranes. Since it is generally desired to provide a circular cross section having a relatively smooth surface, the thicker the membrane, the smaller the surface area will be in practice. Accordingly it will be easy to adjust the release profile, such that one active ingredient e.g. the active ingredient in reservoir 14d, can be released to the surroundings in an ever smaller concentration than the other active ingredients in reservoirs 14a, 14b, and 14c. Thus, again minor or small adjustments to the overall system will alter the release profile significantly.

Figure 8:
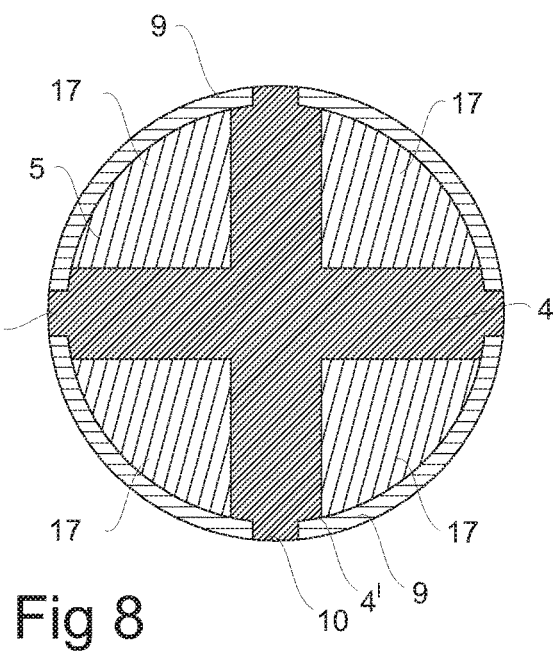
FIG. 8 shows a cross-sectional view of a sixth embodiment of a delivery system according to the present invention.

FIG. 8 shows a cross-sectional view of a sixth embodiment of a delivery system according to the present invention, and the structure corresponds in reality to the embodiment shown in FIG. 4, with the modification that all four reservoirs 17 are identical, and contains the same/identical active ingredient. This solution is advantageous from a production-point of view, since the same supports can be used for several embodiments. In this way the support functions as a universal support, which can be loaded with one or more active ingredients and where each active ingredient is released at a controlled rate. Accordingly, the need to provide an individual inert support designed for a specific application is eliminated.

Figure 9:
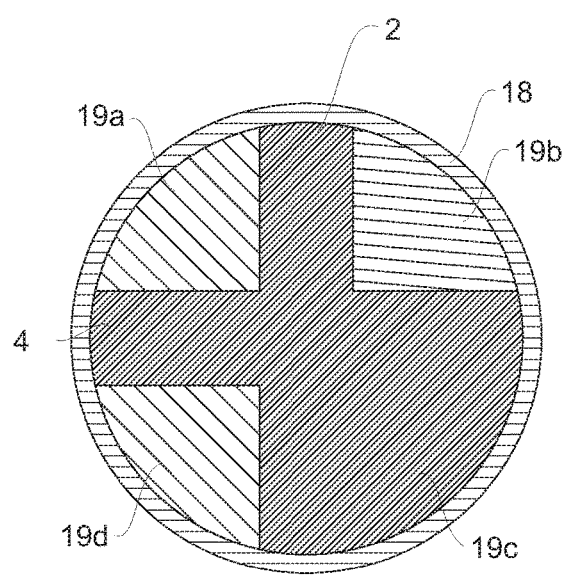
FIG. 9 shows a cross-sectional view of a seventh embodiment of a delivery system according to the present invention.

A cross-sectional view of a seventh embodiment according to the present invention is shown in FIG. 9. Said embodiment differs from the above embodiments in that a single uniform membrane 18 covers the inert support 2 and in that one of the reservoirs 19c, does not contain any active ingredients. In the present embodiment, reservoir 19c without active ingredient, has been added to the inert support when the inert support was manufactured, i.e. one of the compartments was filled with the same material as the remaining of the inert support during the extrusion, such that said reservoir in reality became part of the inert support, i.e. only three compartments was provided for receiving reservoirs. However, this can of course also be achieved by placing a reservoir without active ingredients in said compartment later. Furthermore, more than one compartment can be filled with the same material as the inert support.

The purpose of incorporating one or more reservoirs without active ingredient into the delivery system according to the invention is to provide further alternative for altering and/or adjusting the release profile of the system even further. However, this can also be relevant if specific ratio of the active ingredients can be achieved more economically in this way, or if a higher degree of stiffness/rigidity of the inert support is required.

A single membrane 18 having uniform thickness covers the entire circumference of the inert support 2 and the reservoirs 19a, 19b,19c. Accordingly, the membrane 18 will hold all the reservoirs securely in place. Such an embodiment is very simple and inexpensive, and can also be relevant when the active ingredient in e.g. reservoir 19a and 19d, cannot diffuse in a substantial degree via the membrane into the reservoir 19b, which contains a different active ingredients.

Figure 10:
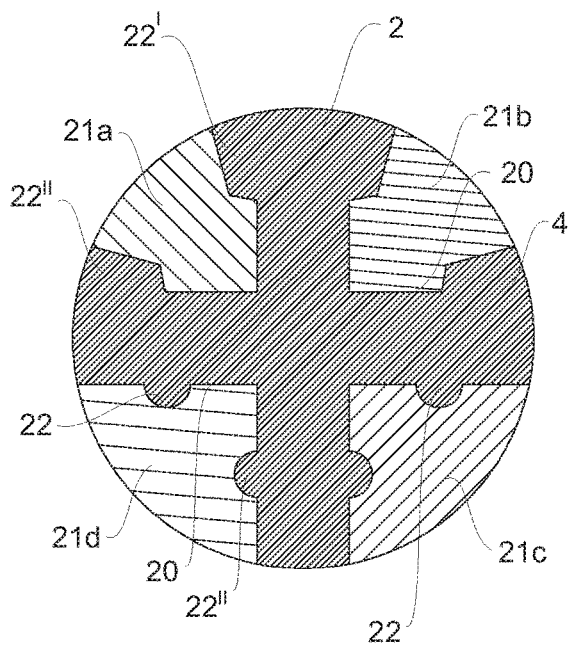
FIG. 10 shows a cross-sectional view of an eight embodiment of a delivery system according to the present invention.

In some situation it can be problematic to maintain the reservoirs in the correct position in the compartment 5, simply because the materials do not adhere securely to each other during manufacture or use. One way of providing a safe and effective adherence of the reservoirs to the support is shown in FIG. 10 in which the side surfaces 20 of the wall segments 4 facing the reservoir 21a, 21b, 21c, and 21d comprises a number of first retention means 22, in the form of barbs 22' and circular projections 22". Said first retention means are made as an integral part of the inert support, however they can also be placed on the relevant side surfaces after the support has been provided e.g. by gluing or melting said first retention means to the support.

It must be noted that if a single membrane covers the system completely as in the embodiments shown e.g. in FIGS. 6 and 9, then said membrane will retain the reservoirs in place, and the need for retention means may be less significant.

Figure 11:
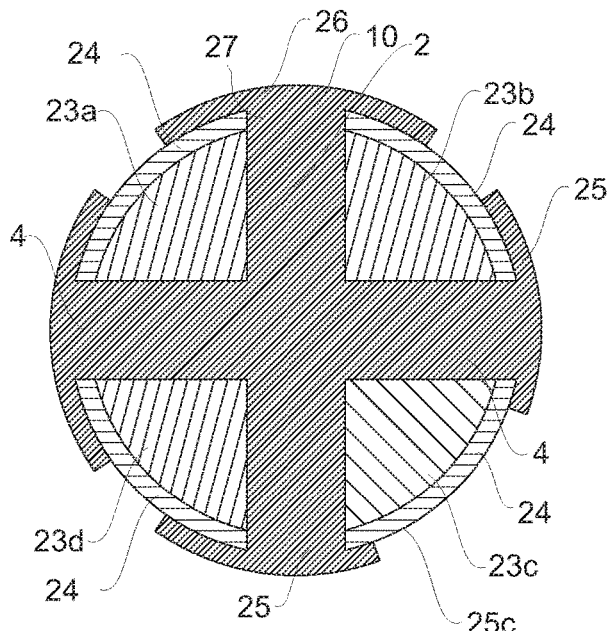
FIG. 11 shows a cross-sectional view of a ninth embodiment of a delivery system according to the present invention.

A cross sectional view of an eight embodiment according to the present invention is shown in FIG. 11. Said embodiment is also arranged for securing the four reservoirs 23a, 23b, 23c, 23d, and the four identical membranes 24 in place. In this embodiment the support 2 comprises at least one second retention means 25, for securing the reservoirs 23 and the rate-controlling membranes 24 to the inert support 2. The second retention means is a projection 25 in the form of a fraction of a circle, placed on the end-surface 26 of at least one of the wall segments 4.

As can be seen in FIG. 11 the projections 25 partly covers the reservoirs 23a, 23b, 23c, 23d and the membranes 24, in such a way that all elements are held securely in place. The projection covers the membranes 24 in varying degrees, thereby providing an additional way of adjusting the release rates of the different active ingredient in the respective reservoirs. In the embodiment shown, the surface area 25c of the membrane though which active ingredient is allowed to diffuse/migrate is larger for reservoir 23c having one active ingredient, than for the identical reservoirs 23a, 23b, 23d accommodating a different active ingredient. Thereby is provided a further means for adjusting the release rate of the active ingredients in the system according to the invention.

Furthermore, the section 27 of the wall segment 4 spanning the membrane, will function as the extension 10, described under FIG. 4, FIG. 5 and FIG. 8, i.e. said section will effectively separate the membranes, preventing any active ingredient from entering the other reservoirs though the membranes.

Figure 12:
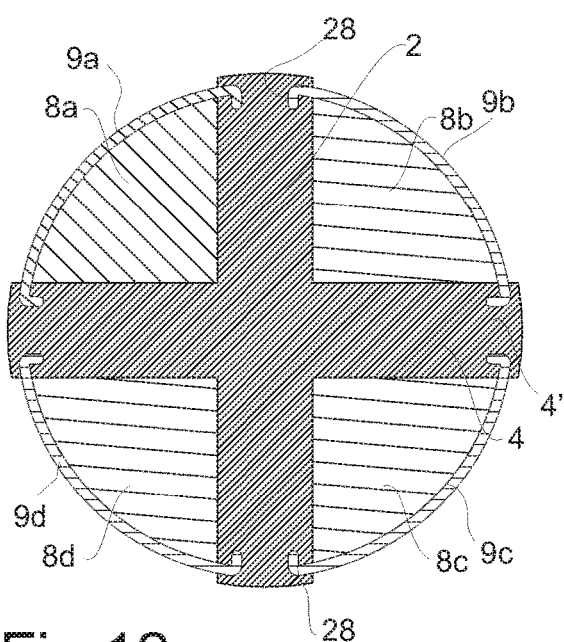
FIG. 12 shows a cross-sectional view of a tenth embodiment of a delivery system according to the present invention, FIG. 13a, 13b, 13c, 13d schematically shows different cross sections of the inert support.

Another way of ensuring that the rate-controlling membranes 9a,9b,9c,9d are effectively and securely held in place is to add third retention means 28 to the membranes, such that they is arranged for being embedded into the end-surfaces of the wall segments, as shown in FIG. 12.

Figure 13A:
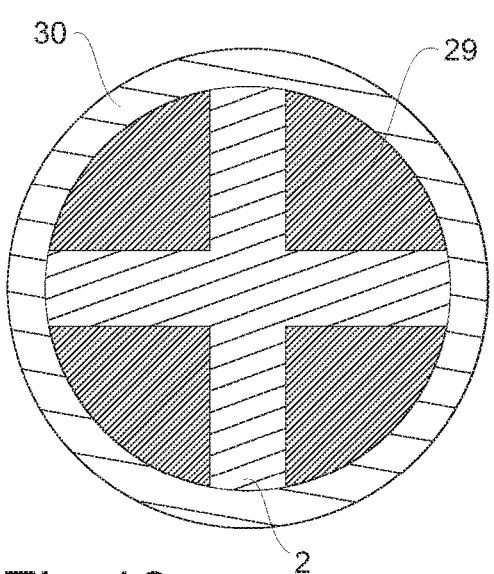
Figure 13B:
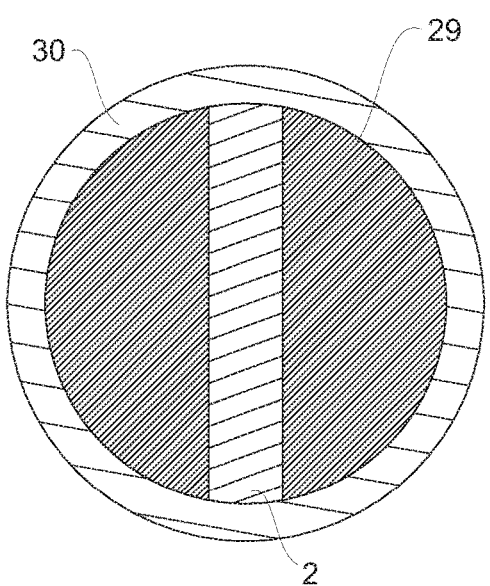
Figure 13C:
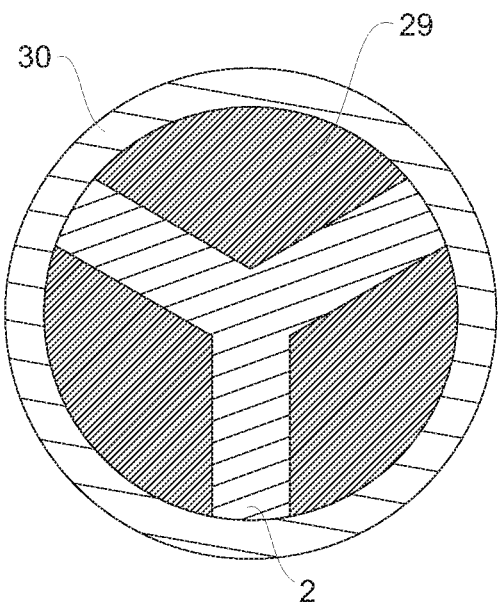
Figure 13D:
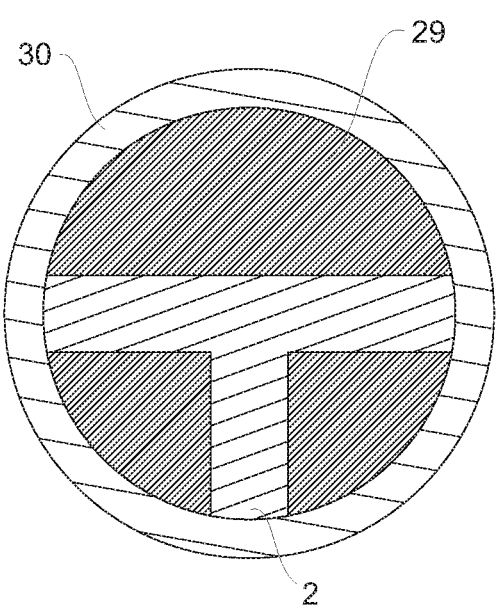

The above embodiments of the delivery system according to the invention, have all been described with a support in the form of an X, having four compartments and accordingly four reservoirs, as shown schematically in FIG. 13a. However as is evident from FIGS. 13b, 13c, and 13d, the support can also have cross-sections in the form of an I, Y, or T, receptively. The person skilled in the art will understand that the support in principal can have any cross-sectional design, and that said inert support can have any preferred number of compartments, as long as the support is arranged for preventing any interference between the reservoirs.

The choice of desired cross-section of the inert support will in any given case depend on the desired ratio of delivery rates of the active ingredient in the reservoirs 29. In this way the present invention resides in a unique means of delivering one, and preferably two or more, active ingredient(s) simultaneously to an environment at a specified ratio of delivery rates.

It is also clear from the figures that the reservoirs of the shown embodiments are held within the boundaries of the inert support 2, such that the reservoirs outer surface does not extend beyond the end surfaces of the wall segments.

In the embodiments shown in FIGS. 13a, 13b, 13c and 13d, the reservoirs 29 are all made of the same material having the same active ingredients, however this can easily be adjusted based on the present application, and must not be constructed as limiting. Similar the membrane 30, which is shown as a single membrane, can be divided into one or more individual membranes, depending one the desired release profile.

It will be understood by a person skilled in the art based on the above invention, that the parameters of the reservoirs and/or the rate controlling membranes can be varied singly or in combination, and further variations may also be incorporated, such as the length of the respective reservoir and the size of the delivery device.

Control of the delivery rates of the active ingredient in the delivery system according the invention, is thus transferred to a number of easily adjustable parameters, which provide a full range of flexibility and variation, rather than relying on the quantities, concentrations, and ratios of the active ingredients or polymers alone. Thereby is obtained a very effective and inexpensive drug delivery system, in which the active ingredients are released in a more controlled manner than hitherto known.

The above embodiments for delivery systems can be used as a drug delivery device, either alone or in combination with other parts of a delivery device.

Figure 14:
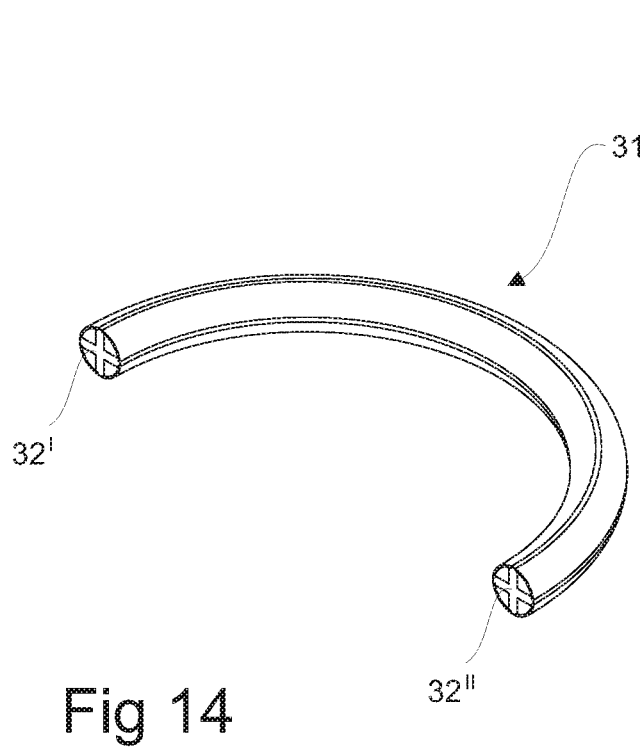
FIG. 14 shows a first embodiment of a delivery device according to the present invention in the form of a section of an intravaginal ring.

In a preferred embodiment the drug delivery device is an intravaginal ring, a segment 31 of which is shown in FIG. 14. The cross sectional design of said segment, corresponds to the embodiment shown in FIG. 4. Said segment has been provided using sequential extrusion, i.e. the support, reservoirs and membranes are extruded in separate extrusion steps, with appropriate curing/cooling steps in-between. Thereby is provided long filaments that can be cut at appropriate lengths into segments 31 for forming the vaginal ring. The two ends of the segments 32' and 32" are thereafter assembled; by connecting them to each another e.g. by gluing or melting; thereby providing a desired vaginal ring structure. In FIG. 14 the segment has been slightly bend and is in the process of being assembled. It will be understood by a person skilled in the art, that during assembly of the ring, corresponding reservoirs are matched in order to prevent migration/diffusion of active ingredients from one reservoir to other reservoirs.

Figure 15:
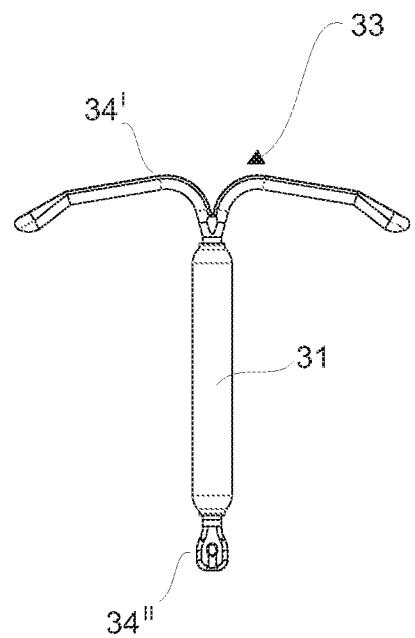
FIG. 15 shows a second embodiment of a delivery device according to the present invention in the form of intrauterine device.

Alternatively, the filaments can be cut into appropriate length for combination with a part of a T-frame, in order to provide a IUD 33, as shown in FIG. 15. Here a segment e.g. the segment 31 shown in FIG. 14 is placed between an upper portion 34' and a lower portion 34" of a conventional T-frame, providing the final IUD.

EXAMPLES

In order to compare the release profiles of a drug delivery system according to the invention with a conventional drug delivery system, six drug delivery systems according to the invention with six different cross sectional designs were constructed, and compared with two conventionally drug delivery systems of two designs. Two units of each system were manufactured, all in the form of vaginal rings.

Construction of Vaginal Rings
Inert Support

The inert support/skeleton of the rings according to the invention, were made of a thermoplastic materials, selected from low density polyethylene (LDPE) obtainable from Celanese Corporation, ethylvinylacetate 9% vinyl acetate (EVA 9% VA), obtainable from Celanese Corporation and ethylvinylacetate 18% vinyl acetate (EVA 18% VA) obtainable from Arkema.

The LDPE skeleton was extruded at 130° C., the EVA 9% VA skeleton was extruded at 110° C., and the EVA 18% VA skeleton was molded.

Reservoir

The reservoirs of the rings according to the invention were made of the polydimethylsiloxanes, MED4-4420 or MED5-6382 obtainable from NuSil Technology LLC. Each reservoir contained a single pharmaceutical active ingredient (API) selected from ethinylestradiol (obtainable from Bayer Pharma AG), levonorgestrel (obtainable from Chemo Group, Spain), and drospirenone (obtainable from Sterling S.p.A.).

MED4-4420 is a platinum catalyzed, addition cure silicone system, and MED5-6382 is a tin catalyzed, condensation cure system.

The respective active ingredients are uniformly suspended as particles throughout the polymer and the reservoirs are matrix systems (monolithic system).

Membrane

The membranes used in the rings according to the invention were made of the polydimethylsiloxanes, MED4-4420 or MED5-6382 obtainable from NuSil Technology LLC. The membranes did not contain any active ingredients.

Ring Construction

The rings according to the invention, ring 1-6, were manufactured by sequential extrusion of the reservoirs onto the skeleton, and when relevant also the membrane, followed by cutting the extruded string in 160 mm sections. The ring form were obtained by melting the ends together (using EVA 18% VA). The joint of ring 2-6 was covered with the same polydimethylsiloxane that was used as an outer layer and/or membrane.

The rings 7-8 that were of the conventional kind had a drug containing core covered by a membrane, and were manufactured using conventional techniques i.e. by first molding the inner ring and then the membrane was overmolded in two steps. Cores and membranes were made of a material identical to the reservoirs and membranes used for the rings according to the invention. The temperatures used are the same as for the rings according to the invention.

All rings were cured at 60° C. for about 1 hour.

Design

Figure 16A:
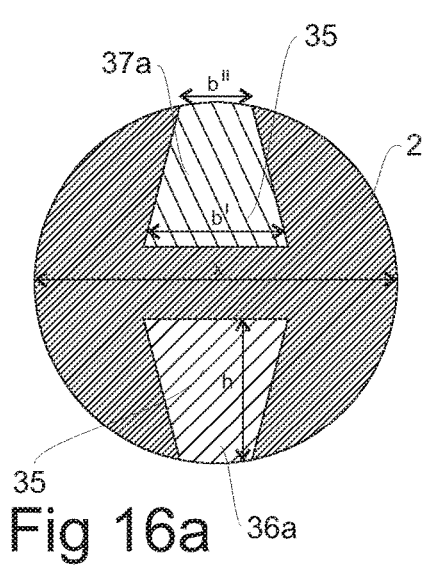
FIG. 16a-16f shows six different ring designs according to the invention, and which has been used in experiments for determining the relate rates of active ingredients.
Figure 16B:
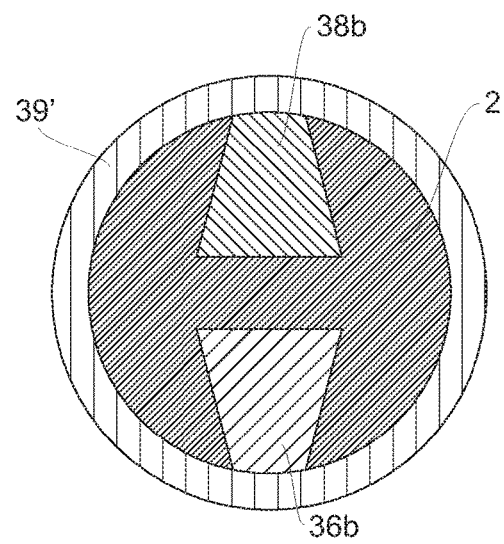
Figure 16C:
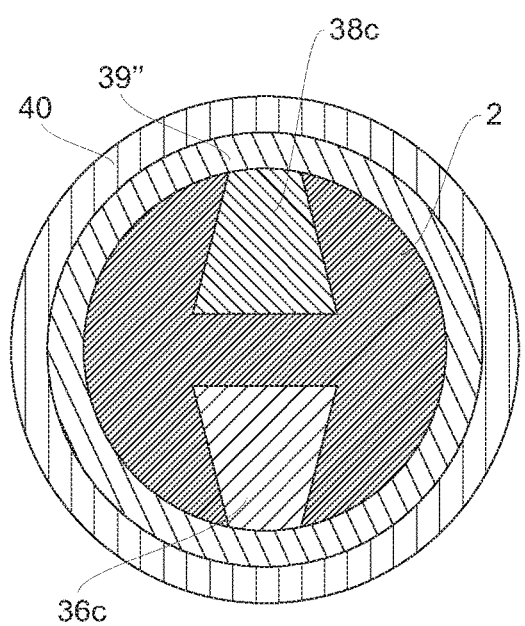
Figure 16D:
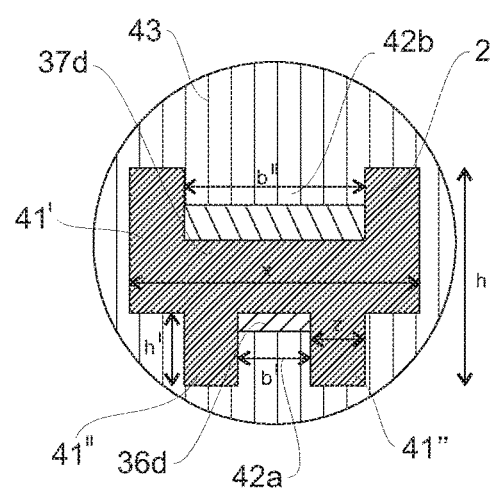
Figure 16E:
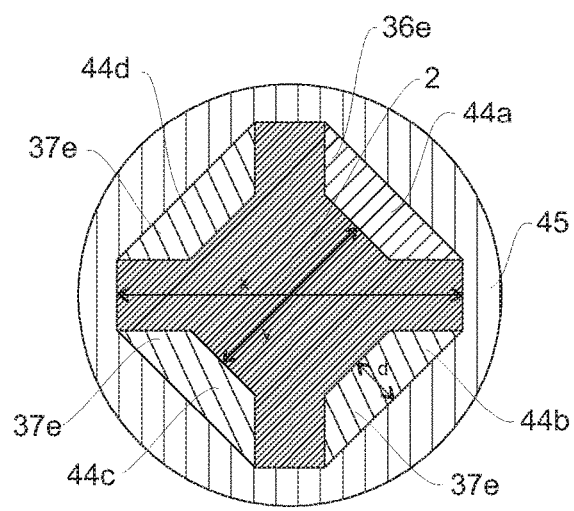
Figure 16F:
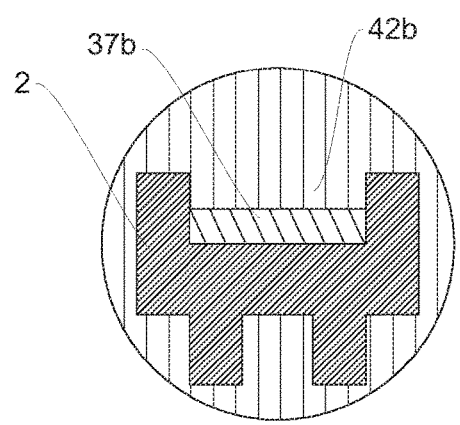
Figure 17A:
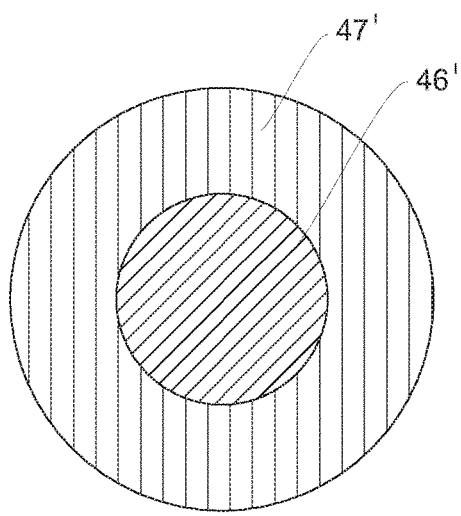
FIG. 17a, 17b shows two conventional ring designs used as in the experiments for determining the relate rates of active ingredients.

The cross-sectional views of the rings 1-6, are shown in FIG. 16a-16f respectively, and the cross-sectional views of conventional ring designs for ring 7 and 8, are shown in FIG. 17a and b.

Ring 1 is shown in FIG. 16a. The inert support 2, has an overall H-shape providing two compartments 35 which is designed such that the both compartments are wider at the base, (i.e closest to the longitudinal axis of the inert support) than at the opening, (i.e. at the surface area not in contact with the inert support). In this way the reservoirs 36a, 37a can easily be retained in the compartment, without any additional means.

Each compartment has a width b' of 1.5 mm at the base and a width b" of 1.0 mm at the opening. The depth h of the compartment is 2.0 mm. The skeleton and string diameter x is 5 mm, and accordingly the device has the same cross-sectional diameter.

The first reservoir, 36a contains 5 w/w % ethinylestradiol in MED5-6385 and the second reservoir 37a contains 20 w/w % drospirenone in MED4-4420.

Ring 2 is shown in FIG. 16b, and has the same skeleton profile as ring 1. As for ring 1, the first reservoir 36b contains 5 w/w % ethinylestradiol in MED5-6382 whereas the second reservoir 38b contains 5 w/w % levonorgestrel in MED5-6382. An 0.5 mm layer 39' of MED5-6382 with 20% drospirenone covers the entire ring. Said layer 39', will both function as a membrane layer for the active ingredients placed in the reservoirs 36b and 38b, and as a drug-containing layer.

Ring 3 is shown in FIG. 16c, and has the same skeleton profile as ring 1 and 2. As for ring 2, the first reservoir 36c contains 5 w/w % ethinylestradiol in MED5-6382 and the second reservoir 38c contains 5 w/w % levonorgestrel in MED5-6382. A 0.5 mm membrane 40 of MED5-6382 covers the entire ring. Between the skeleton/reservoirs construction and the membrane 40, is placed a 0.5 mm drug containing layer 39" of 20 w/w % drospirenone in MED5-6382. Said layer 39", will function both as a membrane layer for the active ingredients placed the reservoirs 36c and 38c, and as a drug-containing layer.

Ring 4 is shown in FIG. 16d. In this ring the inert support 2 has the shape of a U-form 41' with two legs 41", providing a first and second compartment 42a and 42b, respectively. The first compartment 42a has a width b' of 1 mm, the second compartment 42b has a width b" of 2.8 mm. The total width x of the skeleton is 3.8 mm, and the total skeleton height h is 2.5 mm. Each leg 41" has a width z of 0.5 mm and a height h' of 1 mm. In the present case the first compartment 42a is filed to a thickness of 0.2 mm with a first reservoir 36d containing 5 w/w % ethinylestradiol in MED5-6382 and, and the second compartment 42b is filed to a thickness of 0.6 mm with a second reservoir 37b containing 20 w/w % drospirenone in MED5-6382. Thus, none of the compartments are filled completely, as is also evident from the figure. In order to provide a smooth surface of the ring design, an outer membrane 43 is provided. Said membrane is arranged such that it fills the gaps and grooves in the skeleton with the reservoirs. Accordingly, the membrane will be thicker in some places than others, thereby controlling the release rate.

Ring 5 is shown in FIG. 16e. In this ring the inert support 2 has the shape of a filled X, providing four identical compartments 44. The total width and height x of the skeleton is 5 mm and each compartment 44, has a maximum depth d of 0.70 mm. The distance y between the compartments are 2.8 mm. In the present case one compartment 44a is filed with a first reservoir 36e containing 5 w/w % ethinylestradiol in MED5-6382 and, and three compartments 44b,44c,44d are filed with identical reservoirs 37e containing 20 w/w % drospirenone in MED5-6382. An outer membrane 45 is provided, said membrane is arranged such that smooth surface of the ring design is obtained.

Ring 6 is shown in FIG. 16f, and has an inert support identical to the support of ring 4 shown in FIG. 16d, with the modification that no reservoir is present in the first compartment 42a, and that the addition cure silicone, MED4-4420, is used in both reservoir and membrane.

Ring 7 is shown in FIG. 17a, said ring comprises a core 46' of 5 w/w % ethinylestradiol in MED5-6382 having a diameter of 3 mm, covered by a membrane 47' of MED5-6382, providing a total diameter of the string of 6 mm.

Figure 17B:
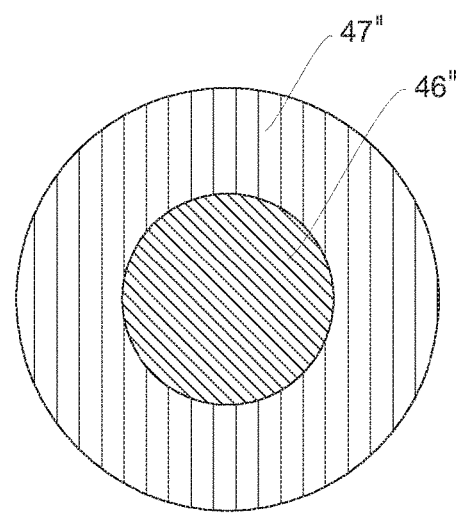

Ring 8 is shown in FIG. 17b, said ring comprises a core 46" of 5 w/w % levonorgestrel in MED5-6382 having a diameter of 3 mm, covered by a membrane 47" of MED5-6382, providing a total diameter of the string of 6 mm Ring Composition The respective rings made according to the invention has the composition shown in table 1, and the conventional rings had the composition shown in table 2.

TABLE 1

| Ring | Skeleton Material | Skeleton Design | Reservoir number | API and reservoir material | Membrane material | String diameter (mm) |
|---|---|---|---|---|---|---|
| 1 | EVA 9% VA | H-form | 2 | 20 w/w % drospirenone in MED4-4420<br>5 w/w % Ethinylestradiol in MED5-6382 | n/a | 5 |
| 2* | EVA 9% VA | H-form | 2 | 5 w/w % levonorgestrel in MED5-6382<br>5 w/w % Ethinylestradiol in MED5-6382 | MED5-6382 | 6 |
| 3** | EVA 9% VA | H-form | 2 | 5 w/w % levonorgestrel in MED5-6382<br>5 w/w % Ethinylestradiol in MED5-6382 | MED5-6382 | 7 |
| 4 | LPDE | U-form with legs | 2 | 20 w/w % drospirenone in MED5-6382<br>5 w/w % Ethinylestradiol in MED5-6382 | MED5-6382 | 5 |
| 5 | EVA 18% VA | X-form | 4 | 20 w/w % drospirenone in MED5-6382<br>5 w/w % Ethinylestradiol in MED5-6382 | MED5-6382 | 6 |
| 6 | LPDE | U-form with legs | 1 | 20 w/w % drospirenone in MED4-4420 | MED4-4420 | 5 |

**Ring 2 contains a drug containing layer of 20 w/w % drospirenone in MED5-6382, covering the skeleton/reservoirs.

**Ring 3 contains a drug containing layer of 20 w/w % drospirenone in MED5-6382, placed between the skeleton/reservoirs, and the membrane.

TABLE 2

| Ring | API and core material | Core diameter (mm) | Membrane material | String diameter (mm) |
|---|---|---|---|---|
| 7 | 5 w/w % Ethinylestradiol in MED5-6382 | 3 | MED5-6382 | 6 |
| 8 | 5 w/w % levonorgestrel in MED5-6382 | 3 | MED5-6382 | 6 |

Drug Release

In vitro release experiments of the active ingredients in the rings were conducted with a typical dissolution test for vaginal rings. The samples were submerged in a glass flask containing 400 ml water medium subjected to shaking of 130 rpm at 37° C., for 14 days. The water medium was exchanged every day except day 4, 5, 11 and 12 (i.e. no change of medium on Saturdays and Sundays). Samples were withdrawn after appropriate time periods, and the concentration of the active ingredients was determined with an HPLC method.

The release rates of the active ingredients of ring 1-8 is shown in table 3 (mean value of two identical rings) for day 1, 2, 7 and 14.

TABLE 3

| | Drug | | | | | | | | | | | |
|---|---|---|---|---|---|---|---|---|---|---|---|---|
| | Drospirenone (µg/day) | | | | Ethinylestradiol (µg/day) | | | | Levonorgestrel (µg/day) | | | |
| Day | 1 | 2 | 7 | 14 | 1 | 2 | 7 | 14 | 1 | 2 | 7 | 14 |
| Ring 1 | 951 | 441 | 265 | 185 | 473 | 260 | 142 | 97 | n.a. | n.a. | n.a. | n.a. |
| Ring 2 | 6677 | 6304 | 5561 | 4556 | 65 | 36 | 37 | 37 | 13 | 8.2 | 11 | 9.6 |
| Ring 3 | 826 | 751 | 839 | 846 | 61 | 33 | 31 | 32 | 15 | 8.4 | 9.3 | 8.8 |
| Ring 4 | 94 | 43 | 48 | 49 | 69 | 36 | 29 | 26 | n.a. | n.a. | n.a. | n.a. |
| Ring 5 | 370 | 316 | 331 | 315 | 101 | 89 | 89 | 85 | n.a. | n.a. | n.a. | n.a. |
| Ring 6 | 136 | 61 | 65 | 64 | n.a. | n.a. | n.a. | n.a. | n.a. | n.a. | n.a. | n.a. |
| Ring 7 | n.a. | n.a. | n.a. | n.a. | 334 | 236 | 227 | 206 | n.a. | n.a. | n.a. | n.a. |
| Ring 8 | n.a. | n.a. | n.a. | n.a. | n.a. | n.a. | n.a. | n.a. | 58 | 51 | 55 | 54 |

Desired release rates of the used active ingredients will always depend on the intended use. As an example could the release rate be: 15 µg/day for ethinylestradiol, 20 µg/day for levonorgestrel, and between 500-2000 µg/day for drospirenone. These release rate must not be construed as limiting, and the desired release rate will among others depend on the desired use of the delivery system. The present examples shown that the drug release rates using a delivery system according to the invention can be chosen within a wide range. However, it will be understood that the release rate of the active ingredients easily can be adjusted according to the invention, e.g. by using different thickness of membranes, and/or different shape and size of the respective reservoirs. The present examples are not intended to resemble usable intravaginal rings, but only to demonstrate that the invention provides the possibility of easily controlling and adjusting the release rate of several active ingredients in a single system.

Ring 1 does not have a membrane or outer layer, and accordingly the drug release rate from the reservoirs drops over time as expected with a matrix design. It must however be stressed that the drop in drug release is less pronounced compared to a conventional monolithic matrix design due to the geometry, i.e. when the drug depletes the diffusion path increases as with the monolithic design but the area does not decrease as much as it would with a conventional monolithic matrix design.

It is further evident from the results for ring 2, that the addition of an outer layer provides a close to constant drug release profile for the two reservoirs. The typical burst effect on day 1 and the fact that the drug release rates drops slowly when the drug depletes is expected. However, the release of ethinylestradiol for ring 2 has much lower release rate compared to the conventional design exemplified by ring 7. Levonorgestrel for ring 2 has also a much lower drug release rate compared to the conventional design exemplified by ring 8.

This lower drug release rate using the ring designs according to the invention is highly desirable and very difficult to obtain using the conventional design, as is evident when comparing the release rates of the two conventional rings with ring 2.

The addition of an additional layer between the skeleton/ reservoirs and the membrane, does not only provide an additional drug but also a thicker membrane, since the membrane of the two reservoirs consists of the combination of the drospirenone layer and the membrane. Compared to ring 2 the ethinylestradiol and levonorgestrel releases through a thicker membrane/layer in ring 3 and consequently has slightly lower drug release rate. The drospirenone from the intermediate layer also releases with close to constant drug release rate as expected from a reservoir design.

Ring 4 is an example of a ring with two reservoirs with different surface area. The compartment have straight walls and the membrane secures that the reservoirs are kept in place. As expected the drospirenone releases much slower in ring 4 compared to ring 3 due to the smaller surface area and also due to the thicker membrane.

Ring 5 is an example of a ring with four compartments. One is filled with an ethinylestradiol matrix and three with drospirenone matrixes. Ethinylestradiol releases faster compared to ring 2, 3 and 4 as expected due to the larger surface area of the ethinylestradiol matrix. The release rate of drospirenone is placed between ring 3 and 4 as expected due to the size of the drospirenone matrix surface area.

Ring 6 is an example of a ring with addition cure silicone as compared to ring 4 that contain condensation cure silicone. The drug release rate is as expected in the same magnitude for ring 4 and 6.

Ring 7 and 8 is example of traditional reservoir design of vaginal rings. They are made with a size to resemble and to fairly compare with ring 1 to 6. It is easy to see that those rings have much faster drug release and is not suitable to achieve the slower drug release that can be obtained with the present invention.

The analytical drug release results show that widely different drug release can be obtained using the drug delivery system according to the invention. The main benefits are:
  Controlled drug release, especially to achieve slow drug release with a long duration.
  Suitable for combining several drugs and control the drug release independently for the different drugs by having separate compartments.
  Complex profile of the skeleton is easy to achieve by extruding the skeleton. (Retention design in ring 1 is expensive to mold but easy to extrude).

In the above the invention has been described with the assumption that the drug delivery device is either a vaginal ring or a hormone spiral. However, this assumption is not to be construed as limiting, and the delivery device can just as easily have a different structure/design, or be a different kind of device, e.g. a single-rod subdermal implant. Using the specific construction of the delivery system according to the invention, it is possible to provide drug delivery devices, e.g IVRs and IUDs capable of providing sustained delivery of one or more active ingredient in a substantially zero order release profile. Such drug delivery devices, has an inexpensive design, and can therefore be used equally well both privately and in medical or hospital facilities.

Modifications and combinations of the above principles and designs are foreseen within the scope of the present invention.

What is claimed is:

1. A drug delivery system comprising an elongated inert support and at least two reservoirs comprising an active medicament, wherein the elongated inert support has a longitudinal axis, is without an active medicament, and comprises a number of wall segments integrally formed into the inert support such that the wall segments and inert support constitute a single coherent unit defining and separating at least two compartments arranged longitudinally along the axis of the support, the at least two compartments displaced around the axis and arranged with one of the wall segments positioned between the at least two compartments for accommodating the at least two reservoirs, wherein the inert support and wall segments that constitute a single coherent unit are made of a material which substantially prevents migration or diffusion of active medicament from one reservoir into another reservoir or into the support, wherein each of the at least two reservoirs includes an outer surface through which the active medicament can diffuse or migrate into surroundings, wherein the outer surface of each of the at least two reservoirs does not extend beyond a perimeter formed about ends of the wall segments of the inert support, wherein the at least two compartments of the inert support are arranged for accommodating the at least two reservoirs without providing an interface between the at least two reservoirs, and for separating the at least two reservoirs chemically and physically, and wherein respective compartments of the inert support have a shape complementary to the at least two reservoirs and vice versa.

2. The drug delivery system according to claim 1, further comprising at least one rate-controlling membrane covering at least one reservoir or each of the at least two reservoirs.

3. The drug delivery system according to claim 2, further comprising at least one first reservoir covered by a first rate-controlling membrane and at least one second reservoir covered by a second rate-controlling membrane, wherein the first and second rate-controlling membranes each have a different permeability or thickness.

4. The drug delivery system according to claim 1, wherein the inert support is made of a first thermoplastic material, and wherein at least one compartment of the inert support is arranged such that the at least one compartment is wider at a base of the at least one compartment than at an opening of the at least one compartment, and wherein the elastic modulus of the drug delivery system is substantially defined by the elastic modulus of the inert support.

5. The drug delivery system according to claim 4, wherein the first thermoplastic material is selected from the group consisting of ethylvinylacetate (EVA), thermoplastic polyurethanes (TPUs), polyethylene (PE), polypropylene (PP), polyamide-imide (PAI), polyamide (PA), cross-linked polyethylene (PEX), thermoplastic elastomers (TPE), thermoplastic vulcanizates (TPVs), Polybutylene terephthalate (PBT), polyester, poly (ethylene terephthalate) (PET) and copolymers made with one or more of the foregoing materials.

6. A method of manufacturing a delivery system according to claim 1, which method comprises:
providing an inert support having a number of wall segments defining at least two compartments along the support, wherein the inert support has a longitudinal axis and the at least two compartments are arranged longitudinally along and displaced around the longitudinal axis with one of the wall segments positioned between the at least two compartments, and placing one reservoir in each of the at least two compartments without providing an interface between reservoirs, wherein each reservoir defines an outer surface through which the active medicament can diffuse or migrate into surroundings and wherein the outer surface of each reservoir does not extend beyond the wall segments of the inert support.

7. The method according to claim 6, which further comprises placing at least one rate controlling membrane on at least one reservoir, wherein each reservoir or the at least one rate-controlling membrane is formed simultaneously.

8. The method according to claim 6, which is carried out by extrusion or injection moulding to obtain the delivery system, wherein the inert support, reservoirs and at least one membrane are extruded directly or by sequential extrusion, and further comprising curing or cooling steps after the providing of the support or placing of reservoirs.

9. The drug delivery system according to claim 1, wherein the wall segments are substantially plate-like structures arranged longitudinally along the axis with each one circumferentially extending from the axis.

10. The drug delivery system according to claim 1, wherein the inert support has a cross-section formed as an I, T, Y, H or X and comprises two, three, four or five wall segments to define two, three, four or five compartments.

11. The drug delivery system according to claim 1, wherein at least one reservoir that is present or that is an integral part of the support does not contain the active medicament.

12. The drug delivery system according to claim 1, wherein the active medicament is the same in at least two reservoirs or in all reservoirs.

13. The drug delivery system according to claim 1, wherein the delivery system has an annular, circular, oval or elliptical cross section with the perimeter providing a smooth outer surface without any extensions, projections or edges.

14. The drug delivery system according to claim 1, wherein the inert support comprises either (a) at least one first retention means for securing at least one reservoir in a compartment or on a side surface of a wall segment that faces the at least one reservoir, (b) at least one second retention means in the form of a projection placed on an end-surface of one of the wall segments to close the at least one reservoir or to be placed upon a rate controlling membrane that is mounted upon the at least one reservoir.

15. The drug delivery system according to claim 1, wherein at least one reservoir or a rate-controlling membrane provided as a wall segment is made of a second thermoplastic material or a thermosetting polymeric material, wherein the second thermoplastic material is selected from the group consisting of cellulose acetate butyrate, cellulose acetate propionate, cellulose acetate, ethyl cellulose, polyvinyl acetate (PVA), poly(ethylene-co-methyl acrylate), ethylene-vinyl acetate (EVA), poly(methyl methacrylate), thermoplastic vulcanizates (TPVs), thermoplastic polyurethanes (TPUs) and copolymers thereof; and wherein the thermosetting polymeric material is polydimethylsiloxane, a silicone polymer with functional phenyl-, fluoro-, chloro-, or butyl groups, or another pharmaceutical acceptable silicone material.

16. The drug delivery system according to claim 1, wherein the active medicament is an estrogenic steroid, a progestational steroid or another contraceptive agent, or is at least one spermicide, an antimicrobial agent or an anti-viral agent.

17. A delivery device comprising the delivery system according to claim 1 and being in the form of an implant, an intrauterine device or a vaginal ring, wherein drug delivery is inert.

18. An inert support that has a longitudinal axis, is without an active medicament, and comprises a number of wall segments integrally formed into the inert support such that the wall segments and inert support constitute a single coherent unit defining and separating at least two compartments arranged longitudinally along the axis of the support, the at least two compartments displaced around the axis and arranged for accommodating at least two reservoirs with one of the wall segments positioned between the at least two compartments, wherein the inert support and wall segments that constitute a single coherent unit are made of a material which substantially prevents migration or diffusion of an active medicament from one reservoir into another reservoir or into the support, wherein an outer surface of each of the at least two reservoirs does not extend beyond a perimeter formed about ends of the wall segments of the inert support, wherein the at least two compartments of the inert support are arranged for accommodating the at least two reservoirs without providing an interface between the at least two reservoirs, and for separating the at least two reservoirs chemically and physically, and wherein respective compartments of the inert support have a shape complementary to the at least two reservoirs and vice versa.

\* \* \* \* \*